United States Patent
Orita et al.

(10) Patent No.: US 9,278,059 B2
(45) Date of Patent: Mar. 8, 2016

(54) EMULSIFIED COSMETIC COMPOSITION

(71) Applicant: Kao Corporation, Chuo-ku, Tokyo (JP)

(72) Inventors: Masanori Orita, Shiroi (JP); Hidehiro Nagasawa, Ichikawa (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 14/397,993

(22) PCT Filed: May 29, 2013

(86) PCT No.: PCT/JP2013/064861
§ 371 (c)(1),
(2) Date: Oct. 30, 2014

(87) PCT Pub. No.: WO2013/180157
PCT Pub. Date: Dec. 5, 2013

(65) Prior Publication Data
US 2015/0133550 A1    May 14, 2015

(30) Foreign Application Priority Data

May 30, 2012 (CN) .......................... 2012 1 0175129

(51) Int. Cl.
| | | |
|---|---|---|
| *A61K 8/37* | (2006.01) | |
| *A61K 8/68* | (2006.01) | |
| *A61K 8/06* | (2006.01) | |
| *A61K 8/33* | (2006.01) | |
| *A61K 8/34* | (2006.01) | |
| *A61K 8/41* | (2006.01) | |
| *A61K 8/44* | (2006.01) | |
| *A61K 8/42* | (2006.01) | |
| *A61Q 19/00* | (2006.01) | |
| *A61K 8/49* | (2006.01) | |

(52) U.S. Cl.
CPC . *A61K 8/375* (2013.01); *A61K 8/06* (2013.01); *A61K 8/33* (2013.01); *A61K 8/34* (2013.01); *A61K 8/37* (2013.01); *A61K 8/41* (2013.01); *A61K 8/42* (2013.01); *A61K 8/44* (2013.01); *A61K 8/4973* (2013.01); *A61K 8/68* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 8,647,649 B2* | 2/2014 | Orita | A61K 8/06 424/401 |
| 2003/0206934 A1 | 11/2003 | Riedel et al. | |
| 2005/0152865 A1 | 7/2005 | Yamamoto et al. | |
| 2007/0104774 A1 | 5/2007 | Kim et al. | |
| 2008/0058400 A1 | 3/2008 | Yang et al. | |
| 2010/0196429 A1 | 8/2010 | Oka et al. | |
| 2012/0108661 A1 | 5/2012 | Orita et al. | |
| 2013/0005835 A1 | 1/2013 | Uyama et al. | |
| 2014/0194522 A1 | 7/2014 | Kaizu et al. | |

FOREIGN PATENT DOCUMENTS

| | | |
|---|---|---|
| FR | 2 794 366 A1 | 9/1999 |
| JP | 2003-171229 A | 6/2003 |
| JP | 2007-022997 A | 2/2007 |
| JP | 2008-056569 A | 3/2008 |
| JP | 2009-051810 A | 3/2009 |
| JP | 2013-018751 A | 1/2013 |
| JP | 2013-053146 A | 3/2013 |
| JP | 2014-108953 A | 6/2014 |
| WO | WO 2011/004589 A1 | 1/2011 |
| WO | WO 2011/114773 A1 | 9/2011 |
| WO | WO 2013/022037 A1 | 2/2013 |

OTHER PUBLICATIONS

International Search Report (ISR) for PCT/JP2013/064861; I.A. fd: May 29, 2013, mailed Aug. 20, 2013, the Japanese Patent Office, Tokyo, Japan.

International Preliminary Report on Patentability (IPRP) including the Written Opinion of the International Searching Authority (PCT Rule 44*bis*) for PCT/JP2013/064861; I.A. fd: May 29, 2013, issued Dec. 2, 2014, by the International Bureau of WIPO, Geneva, Switzerland.

Imokawa, G., "Structure and Function of Intercellular Lipids in the Stratum Corneum," Petrochemistry (Yukagaku), 1995; 44(10):751-766, Japan Oil Chemists' Society, Tokyo, Japan.

Extended European search report, including the supplementary European search report and the European search opinion, dated Oct. 14, 2015, for EP application No. 13796574.5, European Patent Office, Munich, Germany.

* cited by examiner

*Primary Examiner* — Samantha Shterengarts
(74) *Attorney, Agent, or Firm* — Sterne, Kessler, Goldstein & Fox, P.L.L.C.

(57) ABSTRACT

An emulsified cosmetic composition comprising the following ingredients (A), (B), (C), and (D): (A) 0.1% by weight or more and 15% by weight or less of at least one compound selected from the group consisting of a sphingosine or a salt thereof, a pseudo-sphingosine or a salt thereof, and an ionic surfactant, (B) at least one compound selected from the group consisting of a monoglyceryl di-fatty acid ester and a sorbitan di-fatty acid ester, (C) at least one compound selected from the group consisting of a ceramide, an alcohol having 12 to 22 carbon atoms, a monoglyceryl mono-C12 to C22 fatty acid ester, a mono-C12 to C22 alkyl glyceryl ether, and a sorbitan mono-C12 to C22 fatty acid ester, and (D) water, wherein in the ingredients (A), (B), and (C), (1) a weight ratio of (A)/((B)+(C)) is 0.04 or more and 1 or less, (2) a mole fraction of (B)/((B)+(C)) is 0.02 or more and 0.45 or less, and (3) a maximum mole fraction of one compound as a single component in the ingredient (B) and the ingredient (C) is 0.2 or more and 0.8 or less.

12 Claims, No Drawings

EMULSIFIED COSMETIC COMPOSITION

FIELD OF THE INVENTION

The present invention relates to an emulsified cosmetic composition.

BACKGROUND OF THE INVENTION

α-Gel has a hydrate-type crystal structure, which is a lamellar structure. The intercorneocytic lipid present in the horny layer (i.e., the outermost skin layer) generally has the α-gel structure. The intercorneocytic lipid prevents entry of outside substances into the skin as well as transepidermal water loss, and the intercorneocytic lipid itself retains water, whereby the softness and smooth appearance of the skin can be maintained. In the skin, the horny layer retains approximately 33% water in the form of bound water, and the intercorneocytic lipid has been reported to retain approximately 13% bound water (the bound water as stated herein is defined as water constrained by components) (Non Patent Literature 1).

Patent Literature 1 discloses an emulsified composition comprising a ceramide known as an intercorneocytic lipid, and the like. Patent Literature 1 states that an emulsified composition having a high moisturizing effect can be obtained by dispersing a ceramide which forms a lamellar α-gel structure into water. This is intended to allow an easily crystallizable ceramide to have the α-gel structure to thereby enhance flowability and skin penetration.

Meanwhile, Patent Literature 2 discloses a cosmetic composition comprising combination of moisture rich compounds, including a low-molecular-weight compound such as an amino acid and a high-molecular-weight compound such as hyaluronic acid.

CITATION LIST

Non Patent Literature

[Non Patent Literature 1] Genji Imokawa, Journal of Japan Oil Chemists' Society, 44, 10, p. 751-766 (1995)

Patent Literature

[Patent Literature 1] JP-A-2003-171229
[Patent Literature 2] JP-A-2008-56569

SUMMARY OF THE INVENTION

The present invention relates to an emulsified cosmetic composition comprising the following ingredients (A), (B), (C), and (D):

(A) 0.1% by weight or more and 15% by weight or less of at least one compound selected from the group consisting of a sphingosine or a salt thereof, a pseudo-sphingosine or a salt thereof, and an ionic surfactant, (B) at least one compound selected from the group consisting of a monoglyceryl di-fatty acid ester and a sorbitan di-fatty acid ester, (C) at least one compound selected from the group consisting of a ceramide, an alcohol having 12 to 22 carbon atoms, a monoglyceryl mono-C12 to C22 fatty acid ester, a mono-C12 to C22 alkyl glyceryl ether, and a sorbitan mono-C12 to C22 fatty acid ester, and (D) water, wherein in the ingredients (A), (B), and (C), (1) a weight ratio of (A)/((B)+(C)) is 0.04 or more and 1 or less, (2) a mole fraction of (B)/((B)+(C)) is 0.02 or more and 0.45 or less, and (3) a maximum mole fraction of one compound as a single component in the ingredient (B) and the ingredient (C) is 0.2 or more and 0.8 or less.

DETAILED DESCRIPTION OF EMBODIMENTS

Even the composition having the α-gel structure as described in Patent Literature 1 rarely produces high effects, because the α-gel structure is destroyed due to the immediate evaporation of the solvent water after its application to the skin, resulting in the re-solidification of the lipid such as a ceramide. The method using a moisturizing ingredient as described in Patent Literature 2 is less than sufficient in terms of the ability to retain water in use, because the amount of water which can be retained by a compound as a single ingredient is substantially equal to the amount of bound water. Although the lamellar α-gel as described above can be expected to be able to retain water, solid lipid components of the α-gel offer a heavy feeling upon application and produce stickiness. Thus, the solid lipid component cannot produce a favorable feeling upon application. Therefore, a technique of protecting the skin by covering the skin with a lamellar α-gel structure or a composition also excellent in texture has not yet been obtained from the dermatological standpoint.

The present invention relates to an emulsified cosmetic composition which forms a film having a lamellar α-gel structure on the skin surface over a long time after its application to the skin and retains bound water and free water (water which is retained between the layers of the lamellar structure, but is not constrained by components of the lamellar structure) between the layers of the lamellar structure so that water remains on the skin for a long time, resulting in improved conditions of the skin.

The present inventors have found the following: by adjusting (A) one or more compounds selected from the group consisting of a sphingosine, a pseudo-sphingosine, their salts, and an ionic surfactant, (B) one or two or more compound(s) selected from the group consisting of a monoglyceryl di-fatty acid ester and a sorbitan di-fatty acid ester, and (C) one or two or more compound(s) selected from the group consisting of a ceramide, a higher alcohol, a monoglyceryl mono fatty acid ester, a monoalkyl glyceryl ether, and a sorbitan mono fatty acid ester within a specific range, there is obtained an emulsified cosmetic composition which forms a film having a lamellar α-gel structure on the skin surface after its application to the skin to thereby allow water to remain on the skin for a long time, resulting in improved conditions of the skin.

The emulsified cosmetic composition of the present invention can form a soft lamellar α-gel-structured film constituted by a low-molecular-weight compound on the skin surface when applied to the skin and dried. Further, the emulsified cosmetic composition of the present invention can retain water and other active ingredients between the layers of the lamellar α-gel structure. This can be useful in obstruction on the skin and barrier functions of the skin and can further achieve an improved feeling of moisture.

[Ingredient (A)]

The ingredient (A) used in the present invention is one or two or more compound(s) selected from the group consisting of a sphingosine, a pseudo-sphingosine, their salts, and an ionic surfactant. It should be noted that two or more compounds as stated herein indicate that, for example, even when there are two or more compounds which are classified as the same ionic surfactant, it is regarded that they are two or more compounds as long as they have different structures.

Among the compounds of ingredient (A) used in the present invention, examples of the sphingosine and pseudo-sphingosine include a sphingosine represented by formula (1).

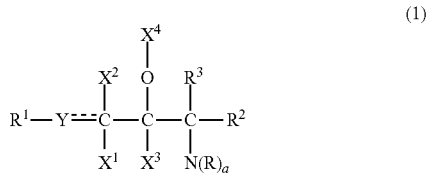

(1)

wherein $R^1$ represents a C4 to C30 linear-chain, branched-chain, or cyclic, and saturated or unsaturated hydrocarbon group which is optionally substituted by a hydroxyl group, a carbonyl group, or an amino group; Y represents a methylene group, a methine group, or an oxygen atom; each of $X^1$, $X^2$, and $X^3$ independently represents a hydrogen atom, a hydroxyl group, or an acetoxy group, $X^4$ represents a hydrogen atom, an acetyl group, or a glyceryl group, or forms an oxo group together with the adjacent oxygen atom (with the proviso that when Y is a methine group, one of $X^1$ and $X^2$ is a hydrogen atom, and the other is absent; and that when $X^4$ forms an oxo group, $X^3$ is absent); each of $R^2$ and $R^3$ independently represents a hydrogen atom, a hydroxyl group, a hydroxymethyl group, or an acetoxymethyl group; each of "R" in $(R)_a$ is independently a hydrogen atom or an amidino group or independently represents a linear-chain or branched-chain, and saturated or unsaturated hydrocarbon group having 1 to 8 carbon atoms in total which optionally has a substituent selected from the group consisting of a hydroxyl group, a hydroxyalkoxy group, an alkoxy group, and an acetoxy group; a represents a number of 2 or 3; and the broken line indicates that a bond between C and Y optionally represents an unsaturated bond.

In the formula, $R^1$ is a C4 to C30 linear-chain, branched-chain, or cyclic, and saturated or unsaturated hydrocarbon group which is optionally substituted by a hydroxyl group, a carbonyl group, or an amino group, preferably a C7 to C22 linear-chain, branched-chain, or cyclic, and saturated or unsaturated hydrocarbon group which is optionally substituted by a hydroxyl group. Particularly, $R^1$ is preferably a C10 to C20 linear-chain or branched-chain alkyl group or a C10 to C20 linear-chain or branched-chain alkyl group having a hydroxyl group at the Y-terminal, and when $R^1$ is a branched-chain alkyl group, for example, one in which the branched-chain is methyl branching is preferable. Specifically, a tridecyl group, a tetradecyl group, a pentadecyl group, a hexadecyl group, a 1-hydroxytridecyl group, a 1-hydroxypentadecyl group, an isohexadecyl group, and an isostearyl group are preferable.

Y represents any of a methylene group ($CH_2$), a methine group (CH), and an oxygen atom.

Each of $X^1$, $X^2$, and $X^3$ independently represents a hydrogen atom, a hydroxyl group, or an acetoxy group, and $X^4$ represents a hydrogen atom, an acetyl group, or a glyceryl group, or a substituent which forms an oxo group together with the adjacent oxygen atom. The sphingosine represented by formula (1) in which 0 to 1 of $X^1$, $X^2$, and $X^3$ is a hydroxyl group and the others are hydrogen atoms and $X^4$ is a hydrogen atom is preferable. It should be noted that when Y is a methine group, only one of $X^1$ and $X^2$ is a hydrogen atom, and the other is absent, and that when $X^4$ forms an oxo group, $X^3$ is absent.

Each of $R^2$ and $R^3$ independently represents a hydrogen atom, a hydroxyl group, a hydroxymethyl group, or an acetoxymethyl group. $R^3$ is preferably a hydrogen atom.

Also, a represents a number of 2 or 3. When a is 2, R represents $R^4$ and $R^5$, and when a is 3, R represents $R^4$, $R^5$, and $R^6$.

Each of $R^4$, $R^5$, and $R^6$ is independently a hydrogen atom or an amidino group, or independently represents a linear-chain or branched-chain, and saturated or unsaturated hydrocarbon group having 1 to 8 carbon atoms in total which optionally has a substituent selected from the group consisting of a hydroxyl group, a hydroxyalkoxy group, an alkoxy group, and an acetoxy group. The hydroxyalkoxy group which optionally substitutes the hydrocarbon group is preferably a C1 to C7 linear-chain or branched-chain hydroxyalkoxy group. The alkoxy group is also preferably a C1 to C7 linear-chain or branched-chain alkoxy group.

Examples of $R^4$, $R^5$, and $R^6$ include a hydrogen atom; a linear-chain or branched-chain alkyl group such as methyl, ethyl, propyl, 2-ethylhexyl, and isopropyl; an alkenyl group such as vinyl and allyl; an amidino group; and a hydrocarbon group having 1 to 8 carbon atoms in total which is substituted by 1 to 6 groups selected from the group consisting of a hydroxyl group, a hydroxyalkoxy group, and an alkoxy group such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxyl)ethyl, 2-methoxyethyl, 1-methyl-2-hydroxyethyl, 3-hydroxypropyl, 3-methoxypropyl, and 1,1-bis(hydroxymethyl)-2-hydroxyethyl.

Among them, a hydrogen atom, methyl or an alkyl group which is optionally substituted by 1 to 3 groups selected from the group consisting of a hydroxyl group and a hydroxyalkoxy group such as 2-hydroxyethyl, 1,1-dimethyl-2-hydroxyethyl, 1,1-bis(hydroxymethyl)ethyl, and 2-(2-hydroxyethoxyl)ethyl is preferable.

The sphingosine represented by formula (1) is preferably a naturally-occurring sphingosine represented by the following formula (2) or a synthetic product having the same structure, or a derivative thereof (hereinafter, collectively referred to as a natural-type sphingosine), or a pseudo-sphingosine having a sphingosine structure represented by formula (3) (hereinafter, referred to as a pseudo-sphingosine).

(I) Natural-type sphingosine represented by formula (2):

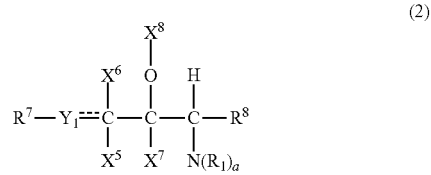

(2)

wherein $R^7$ represents a C7 to C19 linear-chain, branched-chain, or cyclic, and saturated or unsaturated hydrocarbon group which is optionally substituted by a hydroxyl group; $Y_1$ represents a methylene group or a methine group; each of $X^5$, $X^6$, and $X^7$ independently represents a hydrogen atom, a hydroxyl group, or an acetoxy group, and $X^8$ represents a hydrogen atom or forms an oxo group together with the adjacent oxygen atom (with the proviso that when $Y_1$ is a methine group, one of $X^5$ and $X^6$ represents a hydrogen atom, and the other is absent; and that when $X^8$ forms an oxo group, $X^7$ is absent); $R^8$ represents a hydroxymethyl group or an acetoxymethyl group; each of "$R_1$" in $(R_1)_a$ is independently a hydrogen atom or an amidino group or each independently represents a linear-chain or branched-chain, and saturated or unsaturated hydrocarbon group having 1 to 4 carbon atoms in total which optionally has a substituent selected from the group consisting of a hydroxyl group, a hydroxyalkoxy group, an alkoxy group, and an acetoxy group; a represents a number of 2 or 3; and the broken line indicates that a bond between C and $Y_1$ optionally represents an unsaturated bond.

$R^7$ is preferably a C7 to C19 linear-chain, branched-chain, or cyclic, and saturated or unsaturated hydrocarbon group, more preferably a C13 to C15 linear-chain, saturated or unsaturated hydrocarbon group. The "a" is preferably 2, and each of $R_1$s is preferably independently a hydrogen atom or a C1 to C4 linear-chain or branched alkyl group.

Specific examples of the natural-type sphingosine represented by formula (2) include naturally-occurring sphingosine, dihydrosphingosine, phytosphingosine, sphingadienine, dehydrosphingosine, dehydrophytosphingosine, and N-alkyl forms (for example, N-methyl forms) of these sphingosines.

Regarding these sphingosines, either a natural-type optically active form (D(+) form) or a non-natural-type optically active form (L(−) form) may be used. Furthermore, a mixture of a natural-type form and a non-natural-type form may also be used. The relative configuration of the aforementioned compound may be of natural-type, of non-natural-type, or of mixed type.

Among them, phytosphingosine (INCI, 8th Edition) and those represented by the following formulas are more preferable.

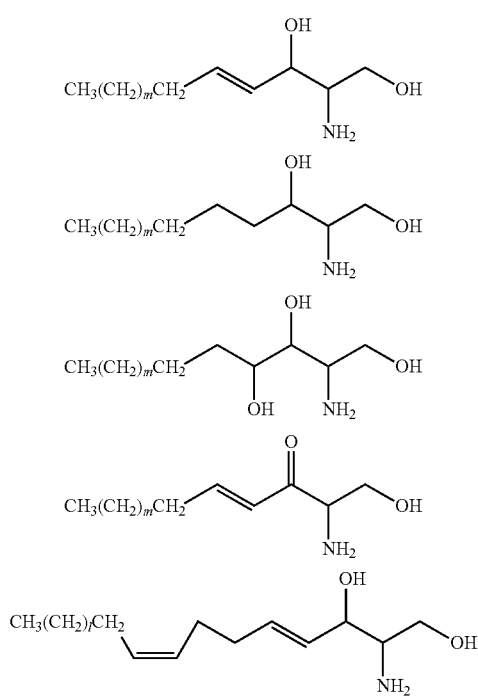

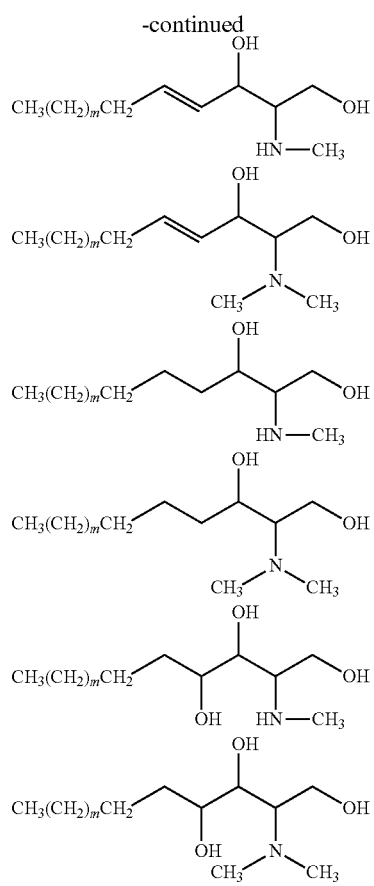

wherein m represents 5 to 17 and l represents 1 to 13.

These sphingosines may be natural extracts or synthetic products. Commercial products thereof may also be employed in the invention. Examples of natural-type sphingosine commercial products include D-Sphingosine (4-Sphingenine) (Sigma-Aldrich Corporation), DS-phytosphingosine (DOOSAN), and phytosphingosine (COSMOFERM).

(II) Pseudo-sphingosine represented by formula (3):

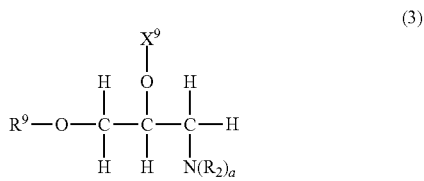

wherein $R^9$ represents a C10 to C22 linear-chain, branched-chain or cyclic, and saturated or unsaturated hydrocarbon group which is optionally substituted by a hydroxyl group; $X^9$ represents a hydrogen atom, an acetyl group, or a glyceryl group; each of $R_2$ in $(R_2)_a$ is independently a hydrogen atom or an amidino group or each independently represents a linear-chain or branched-chain, and saturated or unsaturated hydrocarbon group having 1 to 8 carbon atoms in total which optionally has a substituent selected from the group consisting of a hydroxyl group, a hydroxyalkoxy group, an alkoxy group, and an acetoxy group; and a represents a number of 2 or 3.

$R^9$ is preferably an iso-branched alkyl group having 14 to 20 carbon atoms, and more preferably an isostearyl group.

Specific examples of the pseudo-sphingosine include the following pseudo-sphingosines (i) to (iv):

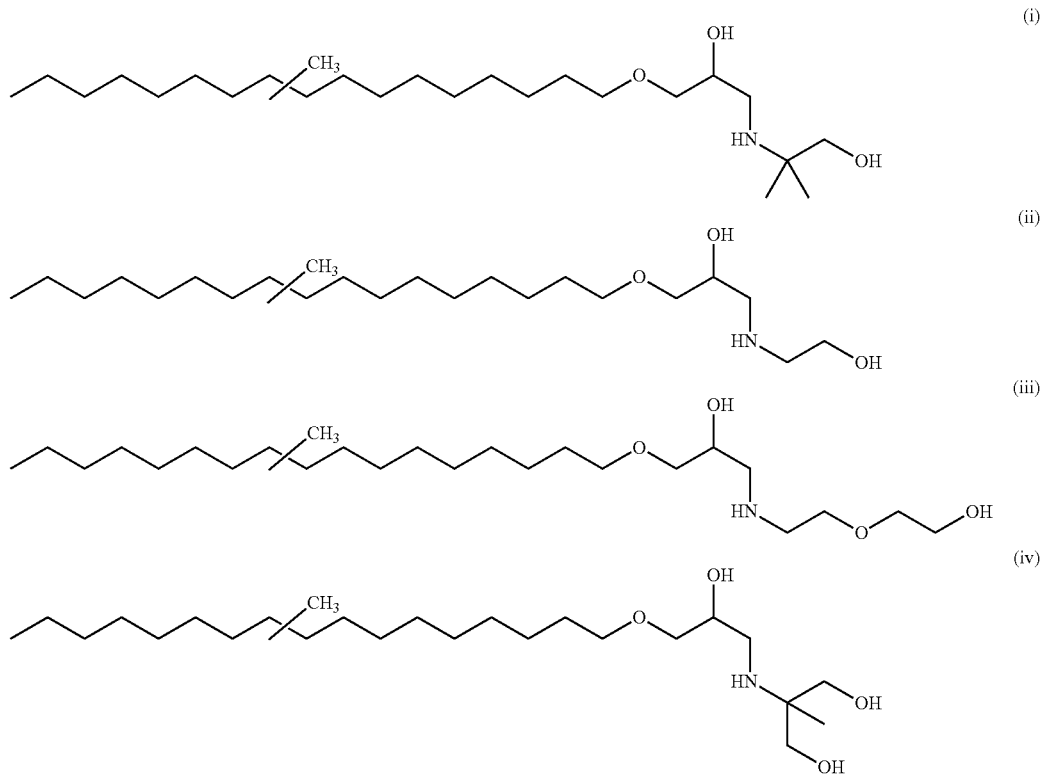

The isostearyl group is even more preferably an isostearyl group obtained from isostearyl alcohol as a raw oil derived from a by-product of dimer acid production using an animal or plant oil-derived fatty acid.

When a is 2, $R_2$ represents $R^{10}$ and $R^{11}$. When a is 3, $R_2$ represents $R^{10}$, and $R^{12}$.

Each of $R^{10}$, $R^{11}$, and $R^{12}$ represents, for example, a hydrogen atom; a linear-chain or branched-chain alkyl group such as methyl, ethyl, propyl, 2-ethylhexyl, and isopropyl; an alkenyl group such as vinyl and allyl; an amidino group; an alkyl group having 1 to 8 carbon atoms in total which optionally has a substituent selected from the group consisting of a hydroxyl group, a hydroxyalkoxy group and an alkoxy group, such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxyl)ethyl, 2-methoxyethyl, 1-methyl-2-hydroxyethyl, 3-hydroxypropyl, 3-methoxypropyl and 1,1-bis(hydroxymethyl)-2-hydroxyethyl.

Among them, a secondary amine is preferable, wherein any one of $R^{10}$ and $R^{11}$ is a hydrogen atom, and the other is 2-hydroxyethyl, 1,1-dimethyl-2-hydroxyethyl, 1,1-bis(hydroxymethyl)ethyl, or 2-(2-hydroxyethoxyl)ethyl.

The pseudo-sphingosine is preferably a pseudo-sphingosine wherein $R^9$ is an isostearyl group; $X^9$ is a hydrogen atom; $R^{10}$ is a hydrogen atom; $R^{11}$ is an alkyl group substituted by 1 to 3 substituents selected from the group consisting of a hydroxyl group and a hydroxyalkoxy group, such as a 2-hydroxyethyl group, a 1,1-bis(hydroxymethyl)ethyl group, a 1,1-dimethyl-2-hydroxyethyl group, or a 2-(2-hydroxyethoxyl)ethyl group.

Examples of salts of these sphingosines and pseudo-sphingosines include a salt with an acidic amino acid such as glutamic acid and aspartic acid; a salt with a basic amino acid such as arginine; a salt with an inorganic acid such as phosphoric acid and hydrochloric acid; a salt with a monocarboxylic acid such as acetic acid; a salt with a dicarboxylic acid such as succinic acid; and a salt with an oxycarboxylic acid such as citric acid, lactic acid, and malic acid. One or two or more selected from the above sphingosine salts are preferable.

Also, among the compounds of the ingredient (A), examples of the ionic surfactant include an anionic surfactant, a cationic surfactant, and an amphoteric surfactant.

Examples of the anionic surfactant include a C12 to C22 fatty acid or a salt thereof such as sodium laurate, potassium palmitate, and arginine stearate; a C12 to C22 alkyl sulfuric acid ester or a salt thereof such as sodium lauryl sulfate and potassium lauryl sulfate; a C12 to C22 alkyl ether sulfuric acid ester or a salt thereof such as polyoxyethylene lauryl sulfate triethanolamine; a N—C12 to C22 acyl sarcosine or a salt thereof such as sodium lauroyl sarcosinate; a C12 to C22 alkyl phosphate or a salt thereof such as sodium monostearyl phosphate; a polyoxyethylene C12 to C22 alkyl ether phosphoric acid or a salt thereof such as sodium polyoxyethylene oleyl ether phosphate and sodium polyoxyethylene stearyl ether phosphate; a C12 to C24 dialkylsulfosuccinic acid or a salt thereof such as sodium di-2-ethylhexyl sulfosuccinate; a C12 to C22 N-alkyloyl methyl taurine or a salt thereof such as sodium N-stearoyl-N-methyl taurate; and a N—C12 to C22-acylglutamic acid or a salt thereof such as sodium dilauroyl glutamate, monosodium N-lauroyl glutamate, sodium N-stearoyl-L-glutamate, arginine N-stearoyl-L-glutamate, sodium N-stearoyl glutamate, and sodium N-myristoyl-L- glutamate. Among them, a C12 to C22 fatty acid or a salt thereof, a polyoxyethylene C12 to C22 alkyl ether phosphoric acid or a salt thereof, a C12 to C22 N-alkyloyl methyl taurine or a salt thereof, and a N—C12 to C22 acylglutamic acid or a salt thereof are preferable.

Further, as the cationic surfactant, a quaternary ammonium salt is preferable. Examples thereof include alkyl trimethyl ammonium chloride such as stearyl trimethyl ammonium chloride and lauryl trimethyl ammonium chloride; dialkyl dimethyl ammonium chloride, ammonium trialkyl methyl chloride, and an alkyl amine salt.

Further, examples of the amphoteric surfactant include alkyl dimethyl amine oxide, alkyl carboxybetaine, alkyl sulfobetaine, an amide amino acid salt, and alkyl amidopropyl betaine, of which alkyl amidopropyl betaine is preferable.

From the viewpoint of emulsification stability, a sphingosine, a pseudo-sphingosine, or their salts and an anionic surfactant are more preferable as the ingredient (A). Among the sphingosine, the pseudo-sphingosine, or their salts, from the economic standpoint, a pseudo-sphingosine (ii) (1-(2-hydroxyethylamino)-3-isostearyloxy-2-propanol or a salt thereof) is preferable. Further, as the anionic surfactant, one or two or more selected from the group consisting of a C12 to C22 fatty acid or a salt thereof, a polyoxyethylene C12 to C22 alkyl ether phosphoric acid or a salt thereof, a sodium C12 to C22 N-alkyloyl methyl taurate, and a N—C12 to C22 acylglutamic acid salt are preferable. From the viewpoint of the feeling upon application, a N—C12 to C22 acylglutamic acid or a salt thereof is more preferable. As the N—C12 to C22 acylglutamic acid salt, N-stearoyl-L-glutamate is preferable, and arginine N-stearoyl-L-glutamate and potassium N-stearoyl-L-glutamate are preferable.

One or more of the ingredients (A) can be used. In more detail, the ingredients (A) can be used alone or in combination of two or more. For example, N-stearoyl-L-glutamic acid salt, 1-(2-hydroxyethylamino)-3-isostearyloxy-2-propanol, sodium POE (4) lauryl ether phosphate, and phytosphingosine can each be used alone. Also, 1-(2-hydroxyethylamino)-3-isostearyloxy-2-propanol can be used in combination with phytosphingosine, and N-stearoyl-L-glutamic acid salt can be used in combination with sodium POE (4) lauryl ether phosphate. Alternatively, sodium dilauroyl glutamate can be used in combination with N-stearoyl-L-glutamic acid salt.

The compound of the ingredient (A) may be used alone or in combination of two or more. The content of the ingredient (A) indicates the content of the compound excluding counterions, and the content of the ingredient (A) in the total composition is 0.1% by weight or more, preferably 0.2% by weight or more, more preferably 0.5% by weight or more. Also, the content thereof is 15% by weight or less, preferably 5% by weight or less, and more preferably 3% by weight or less. These ranges are preferable because each ingredient described later can be stably dispersed and a non-sticky feeling upon application can be obtained. Also, the content of the ingredient (A) in the total composition is from 0.1 to 15% by weight, preferably from 0.2 to 5% by weight, and more preferably from 0.5 to 3% by weight.

[Ingredient (B)]

The ingredient (B) used in the present invention is one or two or more compound(s) selected from the group consisting of a monoglyceryl di-fatty acid ester and a sorbitan di-fatty acid ester. It should be noted that two or more compounds indicate that, for example, even when there are two or more compounds which are classified as a monoglyceryl di-fatty acid ester, it is regarded that they are two or more compounds as long as they have different structures.

A monoglyceryl di-fatty acid ester is preferably a monoglyceryl di-C12 to C22 fatty acid ester, and examples thereof include glyceryl dilaurate, glyceryl dimyristate, glyceryl dipalmitate, glyceryl distearate, glyceryl dibehenate, glyceryl dioleate, and glyceryl diisostearate.

The sorbitan di-fatty acid ester is preferably a sorbitan di-C12 to C22 fatty acid ester. Examples thereof include sorbitan dilaurate, sorbitan dimyristate, sorbitan dipalmitate, sorbitan distearate, sorbitan dibehenate, and sorbitan dioleate.

Among them, from the viewpoint of storage stability, glyceryl distearate and sorbitan distearate are preferable.

The ingredient (B) used in the present invention forms a lamellar structure in combination with the ingredient (A) and the ingredient (C) to be described later. The content of the ingredient (B) is preferably 0.1% by weight or more, more preferably 0.5% by weight or more, and even more preferably 1% by weight or more, and preferably 14.8% by weight or less, more preferably 5% by weight or less, and even more preferably 3.2% by weight or less. Within these ranges, the composition has excellent stability and also reduces stickiness upon application. Also, the content of the ingredient (B) in the total composition is preferably from 0.1 to 14.8% by weight, more preferably from 0.5 to 5% by weight, and even more preferably from 1 to 3.2% by weight.

[Ingredient (C)]

The ingredient (C) used in the present invention is one or two or more compound(s) selected from the group consisting of a ceramide, an alcohol having 12 to 22 carbon atoms, a monoglyceryl mono-C12 to C22 fatty acid ester, a mono-C12 to C22 alkyl glyceryl ether, and a sorbitan mono-C12 to C22 fatty acid ester. It should be noted that two or more compounds indicate that, for example, even when there are two or more compounds which are classified as the same ceramide, it is regarded that they are two or more compounds as long as they have different structures.

Examples of the ceramide of the ingredient (C) used in the present invention include a ceramide represented by formula (4).

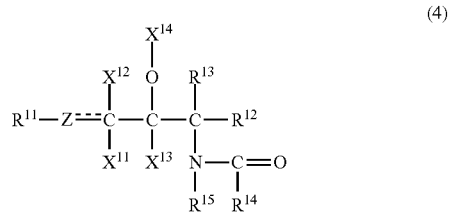

wherein $R^{11}$ represents a C4 to C30 linear-chain, branched-chain, or cyclic, and saturated or unsaturated hydrocarbon group which is optionally substituted by a hydroxyl group, a carbonyl group, or an amino group, or represents a hydrogen atom; Z represents a methylene group, a methine group, or an oxygen atom; each of $X^{11}$, $X^{12}$, and $X^{13}$ independently represents a hydrogen atom, a hydroxyl group, or an acetoxy group, $X^{14}$ represents a hydrogen atom, an acetyl group, or a glyceryl group, or forms an oxo group together with the adjacent oxygen atom (with the proviso that when Z is a methine group, one of $X^{11}$ and $X^{12}$ is a hydrogen atom, and the other is absent; and that when $X^{14}$ forms an oxo group, $X^{13}$ is absent); each of $R^{12}$ and $R^{13}$ independently represents a hydrogen atom, a hydroxyl group, a hydroxymethyl group, or an acetoxymethyl group; $R^{14}$ represents a C5 to C60 linear-chain, branched-chain, or cyclic, and saturated or unsaturated hydrocarbon group which is optionally substituted by a hydroxyl group, a carbonyl group, or an amino group, a main chain of the hydrocarbon group optionally having an ether bonding, an ester bonding, or an amide bonding; $R^{15}$ represents a hydrogen atom or a linear-chain or branched-chain, and saturated or unsaturated hydrocarbon group having 1 to 30 carbon atoms in total which optionally has a substituent selected from the group consisting of a hydroxyl group, a hydroxyalkoxy group, an alkoxy group, and an acetoxy group (with the proviso that when $R^{11}$ is a hydrogen atom and Z is an oxygen atom, $R^{15}$ is a hydrocarbon group having 10 to 30 carbon atoms in total; and that when $R^{11}$ is a hydrocarbon group, $R^{15}$ is a hydrocarbon group having 1 to 8 carbon atoms in total); and the broken line indicates that a bond between C and Z represents an optional unsaturated bond.

In the formula, $R^{11}$ is a C4 to C30 linear-chain, branched-chain, or cyclic, and saturated or unsaturated hydrocarbon group which is optionally substituted by a hydroxyl group, a carbonyl group, or an amino group, preferably a C7 to C22 linear-chain, branched-chain, or cyclic, and saturated or unsaturated hydrocarbon group which is optionally substituted by a hydroxyl group; or a hydrogen atom.

Z represents any of a methylene group, a methine group, and an oxygen atom.

Each of $X^{11}$, $X^{12}$, and $X^{13}$ independently represents a hydrogen atom, a hydroxyl group, or an acetoxy group. It is preferable that none or one of $X^{11}$, $X^{12}$, and $X^{13}$ be a hydroxyl group and the others be hydrogen atoms. When Z is a methine group, then only one of $X^{11}$ and $X^{12}$ is a hydrogen atom, and the other is absent. Also, $X^{14}$ is preferably a hydrogen atom or a glyceryl group.

$R^{12}$ and $R^{13}$ each represent a hydrogen atom, a hydroxyl group, a hydroxymethyl group, or an acetoxymethyl group. $R^{12}$ is preferably a hydrogen atom or a hydroxymethyl group, and $R^{13}$ is preferably a hydrogen atom.

$R^{14}$ represents a C5 to C60 linear-chain, branched-chain, or cyclic, and saturated or unsaturated hydrocarbon group which is optionally substituted by a hydroxyl group, a carbonyl group, or an amino group, wherein the main chain optionally has an ether bonding, an ester bonding, or an amide bonding. Preferable examples of $R^{14}$ include a C5 to C35 linear-chain, branched-chain, or cyclic, and saturated or unsaturated hydrocarbon group which is optionally substituted by a hydroxyl group or an amino group, or the above hydrocarbon group to which a C8 to C22 linear-chain, branched-chain, or cyclic, and saturated or unsaturated fatty acid which is optionally substituted by a hydroxyl group is bonded at the ω position via ester bonding or amide bonding. The fatty acid to be bonded is preferably isostearic acid, 12-hydroxystearic acid, or linoleic acid.

$R^{15}$ represents a hydrogen atom, or a linear-chain or branched-chain, saturated or unsaturated hydrocarbon group having 1 to 30 carbon atoms in total which optionally has a substituent selected from the group consisting of a hydroxyl group, a hydroxyalkoxy group, an alkoxy group, and an acetoxy group. When $R^{11}$ is a hydrogen atom and Z is an oxygen atom, then $R^{15}$ is a hydrocarbon group having 10 to 30 carbon atoms in total. Also, when $R^{11}$ is a hydrocarbon group, $R^{15}$ is a hydrocarbon group having 1 to 8 carbon atoms in total. A hydrogen atom or a hydrocarbon group having 1 to 8 carbon atoms in total which is optionally substituted by 1 to 3 groups selected from the group consisting of a hydroxyl group, a hydroxyalkoxy group, and an alkoxy group is preferable. As the hydroxyalkoxy group and the alkoxy group, those having 1 to 7 carbon atoms are preferable.

The ceramide represented by formula (4) is preferably a ceramide represented by the following formula (5) or (6).

(I) Naturally occurring ceramide represented by formula (5) or a synthetic product having the same structure and derivatives thereof (hereinafter, referred to as natural-type ceramide):

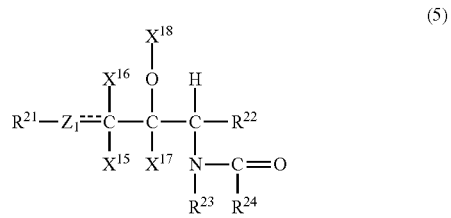

(5)

wherein $R^{21}$ represents a C7 to C19 linear-chain, branched-chain or cyclic, and saturated or unsaturated hydrocarbon group which is optionally substituted by a hydroxyl group; $Z_1$ represents a methylene group or a methine group; each of $X^{15}$, $X^{16}$, and $X^{17}$ independently represents a hydrogen atom, a hydroxyl group, or an acetoxy group; $X^{18}$ represents a hydrogen atom or forms an oxo group together with the adjacent oxygen atom (with the proviso that when $Z_1$ is a methine group, one of $X^{15}$ and $X^{16}$ is a hydrogen atom, and the other is absent; and that when $X^{18}$ forms an oxo group, $X^{17}$ is absent); $R^{22}$ represents a hydroxymethyl group or an acetoxymethyl group; $R^{23}$ represents a hydrogen atom or a C1 to C4 alkyl group; $R^{24}$ represents a C5 to C30 linear-chain, branched-chain, or cyclic, and saturated or unsaturated hydrocarbon group which is optionally substituted by a hydroxyl group, or the above hydrocarbon group to which a C8 to C22 linear-chain or branched-chain, and saturated or unsaturated fatty acid which is optionally substituted by a hydroxyl group is bonded at the ω-end via ester bonding; and the broken line indicates that a bond between C and $Z_1$ represents an optional unsaturated bond.

Preferable examples of the above ceramide include one in which $R^{21}$ is a C7 to C19 (more preferably C13 to C15) linear-chain alkyl group; $R^{24}$ is a C9 to C27 linear-chain alkyl group which is optionally substituted by a hydroxyl group, or a C9 to C27 linear-chain alkyl group to which linoleic acid is bonded via ester bonding. Also, preferably, $X^{18}$ represents a hydrogen atom or forms an oxo group together with an oxygen atom. $R^{24}$ is preferably a tricosyl group, a 1-hydroxypentadecyl group, a 1-hydroxytricosyl group, a heptadecyl group, a 1-hydroxyundecyl group, or a nonacosyl group to which linoleic acid is bonded at the ω-position via ester bonding.

Specific examples of the natural-type ceramide include ceramide Types 1 to 7 in which sphingosine, dihydrosphingosine, phytosphingosine, or sphingadienine is amidated (for example, ceramides of pig and human described in FIG. 2 of J. Lipid Res., 24: 759 (1983), and FIG. 4 of J. Lipid. Res., 35: 2069 (1994)).

The ceramides also encompass N-alkyl forms (e.g., N-methyl form) thereof.

Regarding these ceramides, either a natural-type optically active form (D(−) form) or a non-natural-type optically active form (L(+) form) may be used. Furthermore, a mixture of a natural-type form and a non-natural-type form may also be used. The relative configuration of the aforementioned compound may be of natural-type, of non-natural-type, or of mixed type. Among them, preferred are compounds: CERAMIDE 1, CERAMIDE 2, CERAMIDE 3, CERAMIDE 5, CERAMIDE 6II, (INCI, 8th Edition), and those represented by the following formulas.

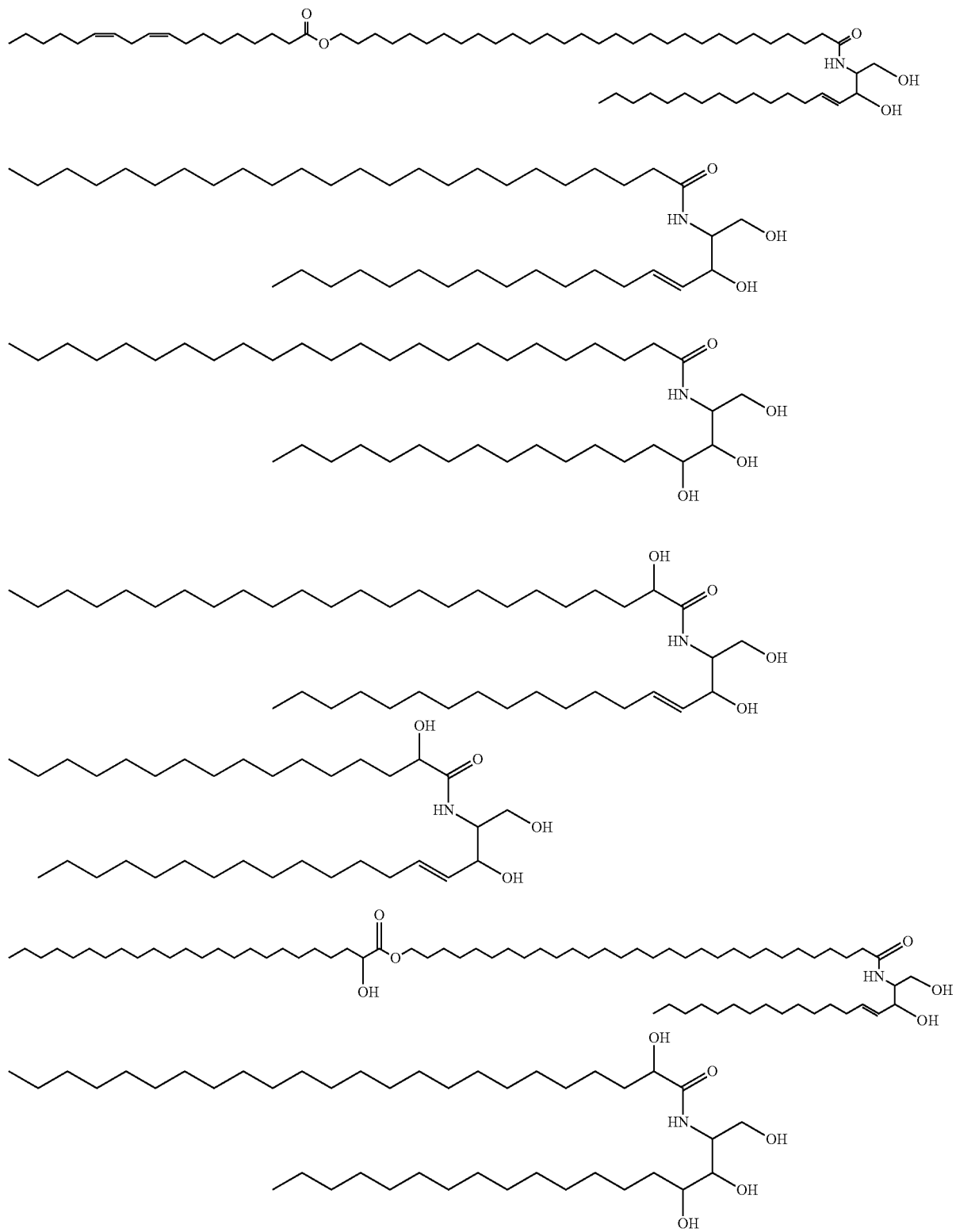

These ceramides may be either natural extracts or synthetic products. Commercial products thereof may also be employed in the invention. Examples of such natural-type ceramide commercial products include Ceramide I, Ceramide III, Ceramide IIIA, Ceramide IIIB, Ceramide IIIC, and Ceramide VI (COSMOFERM); Ceramide TIC-001 (Takasago International Corporation); CERAMIDE II (Quest International); DS-Ceramide VI, DS-CLA-Phytoceramide, C6-Phytoceramide, and DS-ceramide Y3S (DOOSAN); and CERAMIDE 2 (Sederma).

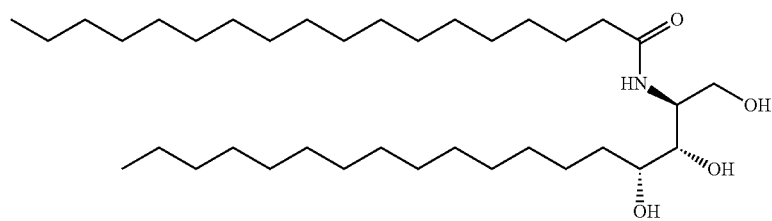
Ceramide III (COSMOFERM)
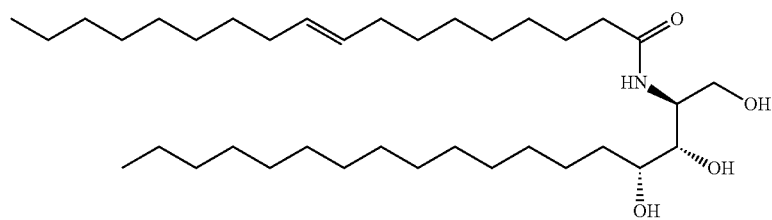
Ceramide IIIB (COSMOFERM)
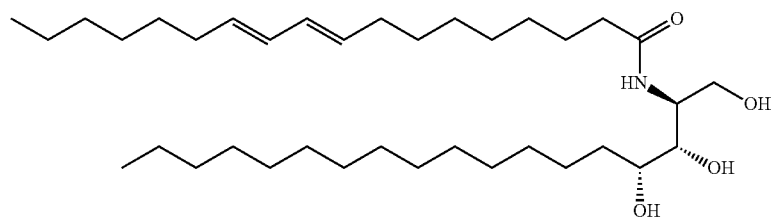
Ceramide IIIB (COSMOFERM)
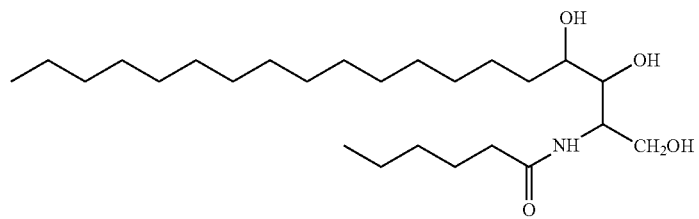
Phytoceramide (DOOSAN)
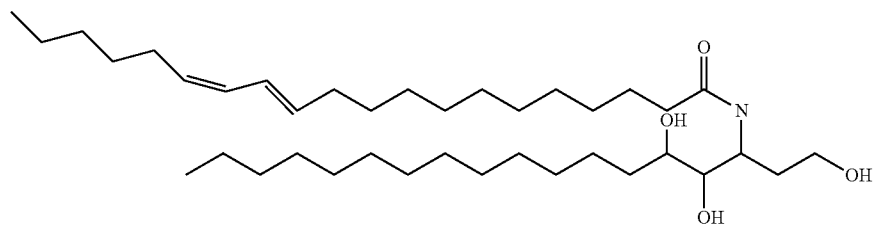
DS-CLA-Phyloceramide (DOOSAN)
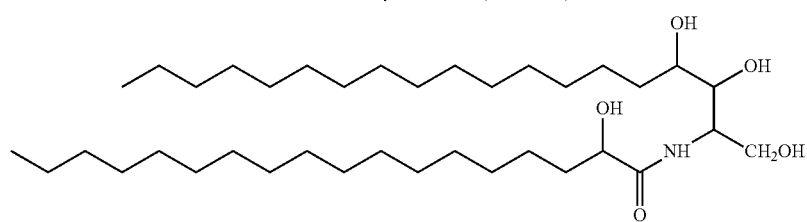
DS-Ceramide VI (DOOSAN)

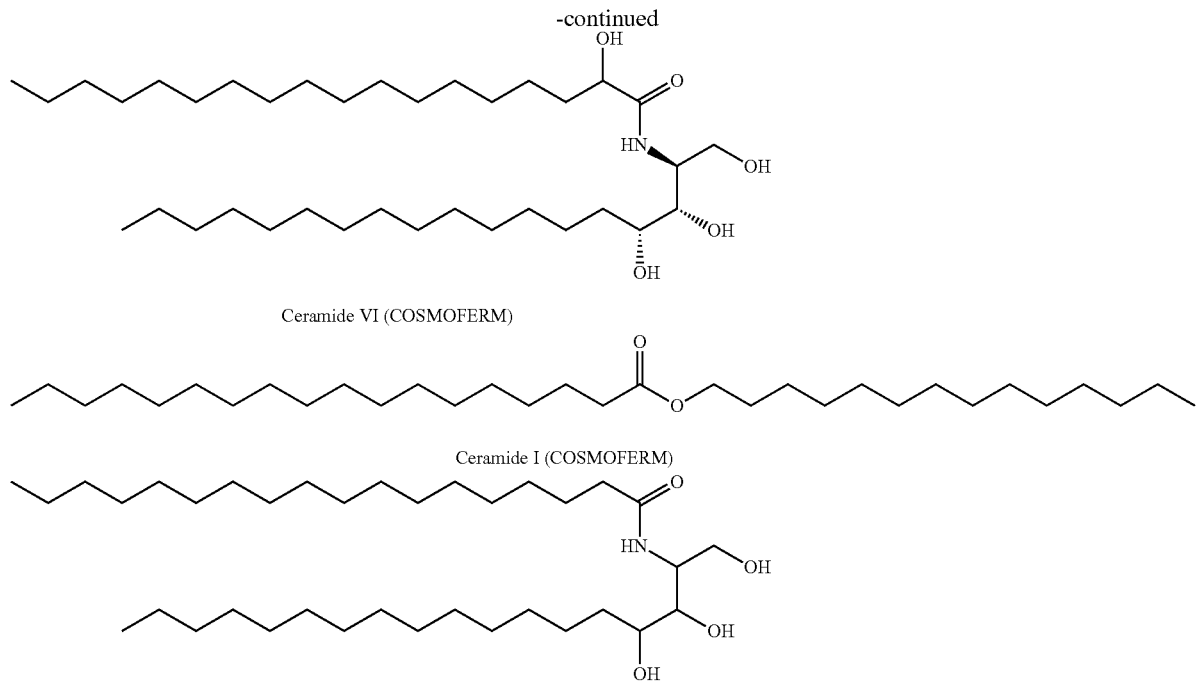

Ceramide VI (COSMOFERM)

Ceramide I (COSMOFERM)

(II) Pseudo-ceramides represented by formula (6):

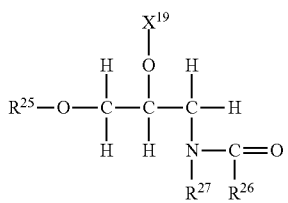

(6)

wherein $R^{25}$ represents a C10 to C22 linear-chain, branched-chain, or cyclic, and saturated or unsaturated hydrocarbon group which is optionally substituted by a hydroxyl group, or represents a hydrogen atom; $X^{19}$ represents a hydrogen atom, an acetyl group, or a glyceryl group; $R^{26}$ represents a C5 to C22 linear-chain, branched-chain, or cyclic, and saturated or unsaturated hydrocarbon group which is optionally substituted by a hydroxyl group or an amino group, or the above hydrocarbon group to which a C8 to C22 linear-chain or branched-chain, and saturated or unsaturated fatty acid which is optionally substituted by a hydroxyl group is bonded at the ω-end via ester bonding; and $R^{27}$ represents a hydrogen atom or an alkyl group having 1 to 30 carbon atoms in total which is optionally substituted by a hydroxyl group, a hydroxyalkoxy group, an alkoxy group, or an acetoxy group.

$R^{26}$ is preferably a nonyl group, a tridecyl group, a pentadecyl group, an undecyl group to which linoleic acid is bonded at the ω-position thereof via ester bonding, a pentadecyl group to which linoleic acid is bonded at the ω-position thereof via ester bonding, a pentadecyl group to which 12-hydroxystearic acid is bonded at the ω-position thereof via ester bonding, or an undecyl group to which methyl-branched isostearic acid is bonded at the ω-position thereof via amide bonding.

Preferably, when $R^{25}$ is a hydrogen atom, $R^{27}$ is an alkyl group having 10 to 30 carbon atoms in total (preferably 12 to 20 carbon atoms in total) which is optionally substituted by a hydroxyl group, a hydroxyalkoxy group, an alkoxy group, or an acetoxy group; and preferably, when $R^{25}$ is a C10 to C22 linear-chain, branched-chain, or cyclic, and saturated or unsaturated hydrocarbon group which is optionally substituted by a hydroxyl group, $R^{27}$ represents a hydrogen atom or an alkyl group having 1 to 8 carbon atoms in total which is optionally substituted by a hydroxyl group, a hydroxyalkoxy group, an alkoxy group, or an acetoxy group. As the hydroxyalkoxy group or the alkoxy group of $R^{27}$, one having 1 to 7 carbon atoms is preferable.

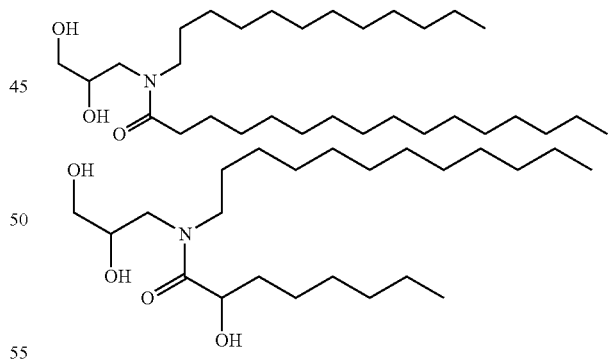

Preferred compound of pseudo-ceramides represented by formula (6) is the case where $R^{25}$ is a hexadecyl group, $X^{19}$ is a hydrogen atom, $R^{26}$ is a pentadecyl group, and $R^{27}$ is a hydroxyethyl group; and the case where $R^{25}$ is a hexadecyl group, $X^{19}$ is a hydrogen atom, $R^{26}$ is a nonyl group, and $R^{27}$ is a hydroxyethyl group. More preferred compound of pseudo-ceramides represented by formula (6) is the case where $R^{25}$ is a hexadecyl group, $X^{19}$ is a hydrogen atom, $R^{26}$ is a pentadecyl group, and $R^{27}$ is a hydroxyethyl group (i.e., N-(hexadecyloxyhydroxypropyl)-N-hydroxyethylhexadecanamide).

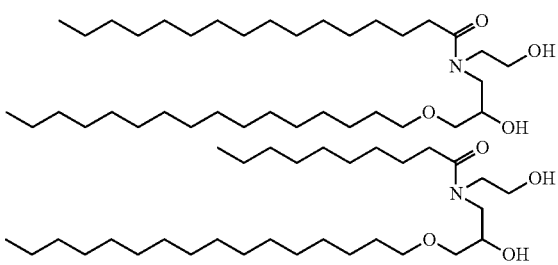

Among the ingredient (C), one or two or more ceramide(s) can be used.

Examples of the alcohol having 12 to 22 carbon atoms of the ingredient (C) include myristyl alcohol, cetanol, stearyl alcohol, behenyl alcohol, and oleyl alcohol. Among them, an alcohol having a linear-chain alkyl group is preferable, an alcohol having 16 to 22 carbon atoms is more preferable, an alcohol having 16 to 18 carbon atoms is even more preferable, and cetanol and stearyl alcohol are further more preferable.

Examples of the monoglyceryl mono-C12 to C22 fatty acid esters of the ingredient (C) include glyceryl monolaurate, glyceryl monomyristate, glyceryl monopalmitate, glyceryl monostearate, glyceryl monobehenate, glyceryl monooleate, and glyceryl monoisostearate. Among them, monoglyceryl mono-C16 to C22 fatty acid esters are preferable, glyceryl monostearate and glyceryl monobehenate are more preferable.

Examples of the mono-C12 to C22 alkyl glyceryl ether of the ingredient (C) include monodecyl glyceryl ether, monolauryl glyceryl ether, monomyristyl glyceryl ether, monocetyl glyceryl ether, monostearyl glyceryl ether, and monobehenyl glyceryl ether. Among them, a mono-C14 to C22 alkyl glyceryl ether is preferable, and monostearyl glyceryl ether is more preferable.

Examples of the sorbitan mono-C12 to C22 fatty acid ester of the ingredient (C) include sorbitan monolaurate, sorbitan monomyristate, sorbitan monopalmitate, sorbitan monostearate, and sorbitan monobehenate. Among them, a sorbitan mono-C14 to C22 fatty acid ester is preferable, and sorbitan monostearate is more preferable.

Among them, in terms of the long-term storage stability and economic standpoint, an alcohol having 16 to 22 carbon atoms, a monoglyceryl mono-C16 to C22 fatty acid ester, a mono-C14 to C22 alkyl glyceryl ether, and a sorbitan mono-C14 to C22 fatty acid ester are preferable as the ingredient (C). Also, an alcohol having 16 to 22 carbon atoms and a monoglyceryl mono-C16 to C22 fatty acid ester are more preferable.

The ingredient (C) used in the present invention forms a lamellar structure in combination with the ingredient (A) and the ingredient (B). The content of the ingredient (C) in the total composition is preferably 0.2% by weight or more, more preferably 0.4% by weight or more, and even more preferably 0.7% by weight or more, and preferably 15% by weight or less, more preferably 12% by weight or less, and even more preferably 5% by weight or less. Within these ranges, the composition has excellent stability and also reduces stickiness upon application. Also, the content of the ingredient (C) in the total composition is preferably from 0.2 to 15% by weight, more preferably from 0.4 to 12% by weight, and even more preferably from 0.7 to 5% by weight.

Also, in the present invention, it is important that the ingredients (A), (B), and (C) satisfy the below-defined relationship:

(1) the weight ratio of A/(B+C) is 0.04 or more and 1 or less,
(2) the mole fraction of B/(B+C) is 0.02 or more and 0.45 or less, and
(3) the maximum mole fraction of one compound as a single component in the components constituting the ingredient B and the ingredient C is 0.2 or more and 0.8 or less.

The weight ratio of A/(B+C) as defined in (1) shows a range within which the ingredient (A) can stably emulsify the ingredients (B) and (C). Also, at such a weight ratio, the molecular arrangement formed by the ingredients (B) and (C) is maintained by electrostatic repulsion. This is important for forming a lamellar film. Further, when the composition of the present invention is applied to the skin, the above weight ratio plays a role of retaining water of the ingredient (D). This is important for maintaining the softness of the lamellar film formed on the skin surface. From the above viewpoints, the weight ratio of A/(B+C) is 0.04 or more and 1 or less, preferably 0.5 or less, and more preferably 0.33 or less.

The mole fraction of (B)/((B)+(C)) as defined in (2) is considered to be important for the molecular arrangement formed by the ingredients (B) and (C) to form a lamellar structure. From the above viewpoint, the mole fraction of B/(B+C) is 0.02 or more and 0.45 or less, preferably 0.4 or less, and more preferably 0.35 or less.

The maximum mole fraction of one compound as a single component in the ingredient B and the ingredient C as defined in (3) is considered to be necessary for the molecular arrangement formed by the ingredients (B) and (C) to form a lamellar structure and for the resulting lamellar structure to be stabilized. In more detail, it is assumed that, when a lamellar structure is formed, such a mole fraction as defined in (3) plays a role of preventing crystallization of ingredients within the lamellar structure, and further, enhancing flowability of molecules in the lamellar structure to maintain the softness of the film formed on the skin. Further, storage stability is also improved. From the above viewpoints, the maximum mole fraction of one compound as a single component in the ingredient (B) and the ingredient (C) is 0.2 or more and 0.8 or less, preferably 0.75 or less, and more preferably 0.7 or less. Also, from the same viewpoints, the component of each of the ingredients (B) and (C) is preferably one compound species or a mixture of two or more compound species, and the total number of compound species constituting the ingredients (B) and (C) is preferably three or more, and more preferably four or more.

Further, with regard to the content of the ingredients (B) and (C), from the viewpoint of the moisturizing effect and storage stability, the total content (B)+(C) of the ingredients (B) and (C) in the total composition is preferably 0.5% by weight or more, and more preferably 1% by weight or more. Also, the total content of the ingredients (B) and (C) in the total composition is preferably 17% by weight or less, more preferably 10% by weight or less, and even more preferably 7% by weight or less. Also, the total content of the ingredients (B) and (C) (ingredient (B)+ingredient (C)) in the total composition is preferably from 0.5 to 17% by weight, more preferably from 1 to 17% by weight, even more preferably from 1 to 10% by weight, and further more preferably from 1 to 7% by weight.

In the present invention, when the ingredients (B) and (C) are composed of two or three or more compounds available as the aforementioned ingredients, the average critical packing parameter of the ingredients (B) and (C) is preferably 0.85 or more, more preferably 0.89 or more, and even more preferably 0.93 or more, and preferably 1.1 or less, more preferably 1.07 or less, and even more preferably 1.06 or less, for an improved ability to retain water and improved obstruction. Also, the average critical packing parameter of the ingredients (B) and (C) is preferably from 0.85 to 1.1, more preferably from 0.89 to 1.07, and even more preferably from 0.93 to 1.06.

The average critical packing parameter of the ingredients (B) and (C) refers to the total sum of values obtained by multiplying the critical packing parameter of each compound by the mole fraction of each compound, provided that the total mole fraction of the compounds constituting the ingredients (B) and (C) is defined as 1.

The "critical packing parameter" is defined as $v/(1 \cdot a)$ wherein v represents the volume occupied by the hydrophobic group in the micellar core; 1 represents the length of the hydrophobic group; and a represents the area occupied by the hydrophilic group at the micelle-solution interface. The critical packing parameter (hereinafter, also referred to as "CPP") is a general parameter for describing the relationship between a molecular structure and an association structure. Israelachvili shows the relationship of the critical packing parameter with a possible stable association structure ("Intermolecular and Surface Forces, with Applications to Colloidal and Biological Systems" Academic Press, London, 1985, p. 247; "Intermolecular and Surface Forces" Second Edition, J. N. Israelachvili, translated by Tamotsu Kondo and Hiroyuki Oshima, Asakura Publishing Co., Ltd., 1996, p. 368; and "Surfactants and Interfacial Phenomena" M. J. Rosen, translated by Kazuyuki Tsubone and Kazutami Sakamoto, Fragrance Journal Ltd., 1995, p. 116).

In the abovementioned definition of the critical packing parameter, when the ratio v/1 (the volume occupied by the hydrophobic group/the length of the hydrophobic group) is referred to as the "cross-sectional area occupied by the hydrophobic group" for the sake of convenience, the critical packing parameter refers to (the cross-sectional area occupied by the hydrophobic group/the area occupied by the hydrophilic group). It is known that, in a single surfactant solution, inverted micelle tends to be formed when the cross-sectional area occupied by the hydrophobic group is larger; on the contrary, micelle tends to be formed when the area (a) occupied by the hydrophilic group is larger; and further, a lamellar structure tends to be formed when the critical packing parameter is around 1 where the hydrophobic group and the hydrophilic group are well-balanced.

In the present invention, the average critical packing parameter was calculated as follows.

The cross-sectional area (v/1) occupied by the hydrophobic group can employ a cross-sectional area of 19.5 square angstroms per alkyl chain in a direction perpendicular to the molecular axis in the α crystal of an aliphatic alcohol, and can be determined, in the case of branched alkyl chains, by multiplying this by a correction factor (the total number of carbon atoms in the alkyl chains/the number of carbon atoms in the largest length of the alkyl chain).

The cross-sectional area (a) occupied by the hydrophilic group can be determined by procedures as described below.

Possible conformations of molecules in which an alkyl chain has been replaced with the shortest methyl group are searched for, and their conformational energies are calculated and arranged in order of what is stable. Software such as Conflex (manufactured by CONFLEX Corp.) can be used for calculation in the conformational search.

From among these conformations, one suitable for arrangement at the interface, i.e., one having a smaller cross-sectional area in the longitudinal direction of the molecule and a lower energy in a hydrated state, is selected. Since the structure suitable for the hydration of polyoxyethylene chains is the 7/2 helix, its conformation is utilized. The energy in the hydrated state can be calculated by use of a method such as the COSMO method (A. Klamt and G. Schuurmann, J. Chem. Soc. Perkin Trans., 2 (1993) 799).

The van der Waals' cross-sectional area of only the hydrophilic group when the molecule is projected in the longitudinal direction is calculated and used as the cross-sectional area (a) occupied by the hydrophilic group. The long axis of the molecule can be determined by the calculation of the moment of inertia in the molecular system. The van der Waal's cross-sectional area can be calculated as follows: a rectangle circumscribing the cross-section of the molecule is defined, and the van der Waal's cross-sectional area is determined from the ratio of points belonging to the cross-section of the molecule to points randomly generated within the rectangle by random numbers using the so-called Monte Carlo method.

In the case of using two or more compounds as the ingredient (B), an average of their critical packing parameters is used as the critical packing parameter of the ingredient (B). The average can be calculated according to the mole fractions of two or more compounds used. For example, in the case of using two compounds, i.e., ingredient B1 and ingredient B2, the average critical packing parameter of the ingredients (B) is calculated according to the following expression:

Average critical packing parameter=Critical packing parameter of the ingredient $B1 \times$Mole fraction of the ingredient B1+Critical packing parameter of the ingredient B2×Mole fraction of the ingredient $B2$.

Water of the ingredient (D) is used as a solvent in the emulsified cosmetic composition. The content thereof in the total composition is preferably 50% by weight or more, and more preferably 60% by weight or more, and preferably 98% by weight or less, and more preferably 95% by weight or less, which forms the balance of the emulsified cosmetic composition other than the aforementioned ingredients and other ingredients constituting the composition. Also, the content of water of the ingredient (D) in the total composition is preferably from 50 to 98% by weight, and more preferably from 60 to 95% by weight.

The emulsified cosmetic composition of the present invention can further comprise a polyhydric alcohol as an ingredient (E). The polyhydric alcohol is capable of improving the softness of the film formed on the skin surface when the emulsified cosmetic composition is applied to the skin.

Examples of the polyhydric alcohol include glycerol, diglycerol, polyethylene glycol, 1,3-butyrene glycol, isoprene glycol, propylene glycol, and dipropylene glycol.

From the viewpoint of the storage stability and feeling upon application, the above content in the total composition is preferably 1% by weight or more, more preferably 5% by weight or more, and preferably 30% by weight or less, more preferably 20% by weight or less. Also, the content of the polyhydric alcohol in the total composition is preferably from 1 to 30% by weight, more preferably from 5 to 20% by weight.

The emulsified cosmetic composition of the present invention can further comprise an oily ingredient as an ingredient (F). The oily ingredient is capable of improving the softness and smoothness of the film formed on the skin surface when the emulsified cosmetic composition is applied to the skin.

Examples of the oily ingredient other than the aforementioned ingredients include a hydrocarbon oil such as liquid paraffin, squalane, and Vaseline; an ether oil such as cetyl dimethylbutyl ether, ethylene glycol dioctyl ether, and glycerol monooleyl ether; an ester oil such as octyldodecyl myristate, isopropyl palmitate, butyl stearate, di-2-ethylhexyl adipate, neopentyl glycol dicaprate, trioctanoin, and a vegetable oil such as an olive oil; a higher fatty acid such as stearic acid, behenic acid, and isomyristic acid; a silicone oil such as dimethylpolysiloxane, cyclic dimethylpolysiloxane, methyl phenyl polysiloxane, amino-modified silicone, carboxy-modified silicone, alcohol-modified silicone, alkyl-modified silicone, polyether-modified silicone, and fluorine-modified silicone; and a fluorine oil such as perfluoroalkyl ethyl phosphate, perfluoroalkyl polyoxyethylene phosphate, perfluoropolyether, and polytetrafluoroethylene.

These oily ingredients can be used alone or in combination of two or more. From the viewpoint of storage stability, the content of the oily ingredient in the total composition is preferably 1% by weight or more, preferably 20% by weight or less, and more preferably 15% by weight or less. Also, the content of the oily ingredient in the total composition is preferably from 1 to 20% by weight, more preferably from 1 to 15% by weight.

The emulsified cosmetic composition of the present invention can further comprise a sterol as an ingredient (G). Examples of the sterol include cholesterol and phytosterol. The phytosterol is a generic name of plant-derived sterols including β-sitosterol, campesterol, stigmasterol, and brassicasterol, and is not limited by its composition.

These ingredients can be used alone or in combination of two or more. From the viewpoint of enhancing the ability to retain water, the content thereof in the total composition is preferably 0.01% by weight or more, and more preferably 0.1% by weight or more, and preferably 2% by weight or less, and more preferably 0.5% by weight or less. Also, the content of the sterol in the total composition is preferably from 0.01 to 2% by weight, and more preferably from 0.1 to 0.5% by weight.

Also, the emulsified cosmetic composition of the present invention can comprise an active ingredient and an additive which are used in common cosmetic compositions, for example, water-soluble vitamins such as ascorbic acid, nicotinamide, and nicotinic acid; an animal or plant extract such as Phellodendron Amurense extract, licorice extract, aloe extract, field horsetail extract, tea extract, cucumber extract, clove extract, ginseng extract, witch hazel extract, placenta extract, seaweed extract, horse chestnut extract, Japanese citron (yuzu) extract, false-arborvitae tree extract, royal jelly extract, Eucalyptus extract, and false-arborvitae tree extract; bases such as potassium hydroxide, sodium hydroxide, triethanolamine, and sodium carbonate; acids such as citric acid, tartaric acid, lactic acid, phosphoric acid, succinic acid, and adipic acid; and a thickening agent such as a carboxy vinyl polymer, sodium alginate, carrageenan, carboxymethyl cellulose, hydroxyethyl cellulose, guar gum, xanthan gum, carboxymethyl chitosan, sodium hyaluronate, oxazoline-modified silicone, and a N,N-dimethylaminoethyl methacrylate diethyl sulfate/N,N-dimethylacrylamide/polyethylene glycol dimethacrylate copolymer.

The emulsified cosmetic composition of the present invention has the α-gel structure (α-type crystal), whereby the precipitation of the crystals (γ-type crystals) is prevented. The α-gel can be confirmed by X-ray structural analysis to be described later.

The emulsified cosmetic composition of the present invention relates to use for moisturizing the skin, comprising applying the emulsified cosmetic composition to the skin and then letting it to dry to thereby form a film having an α-gel structure on the skin surface.

The emulsified cosmetic composition of the present invention relates to a method for moisturizing the skin, comprising applying the composition to the skin and then letting it to dry to thereby form a film having the α-gel structure on the skin surface.

The emulsified cosmetic composition of the present invention relates to use for the production of a skin moisturizer.

In connection with the aforementioned embodiments, the present invention further discloses the following compositions, production methods, or uses.

[1] An emulsified cosmetic composition comprising the following ingredients (A), (B), (C), and (D):

(A) 0.1% by weight or more and 15% by weight or less of at least one compound selected from the group consisting of a sphingosine or a salt thereof, a pseudo-sphingosine or a salt thereof, and an ionic surfactant, (B) at least one compound selected from the group consisting of a monoglyceryl di-fatty acid ester and a sorbitan di-fatty acid ester, (C) at least one compound selected from the group consisting of a ceramide, an alcohol having 12 to 22 carbon atoms, a monoglyceryl mono-C12 to C22 fatty acid ester, a mono-C12 to C22 alkyl glyceryl ether, and a sorbitan mono-C12 to C22 fatty acid ester, and (D) water, wherein, in the ingredients (A), (B), and (C), (1) a weight ratio of (A)/(B+C) is 0.04 or more and 1 or less, (2) a mole fraction of (B)/(B+C) is 0.02 or more and 0.45 or less, and (3) a maximum mole fraction of one compound as a single component in the ingredient (B) and the ingredient (C) is 0.2 or more and 0.8 or less.

[2] The emulsified cosmetic composition according to [1], wherein the emulsified cosmetic composition of the present invention comprises the following ingredients (A), (B), (C), and (D):

(A) preferably 0.1% by weight or more, more preferably 0.2% by weight or more, and even more preferably 0.5% by weight or more, and preferably 15% by weight or less, more preferably 5% by weight or less, and even more preferably 3% by weight or less of at least one compound selected from the group consisting of a sphingosine or a salt thereof, a pseudo-sphingosine or a salt thereof, and an ionic surfactant, (B) preferably 0.1% by weight or more, more preferably 0.5% by weight or more, and even more preferably 1% by weight or more, and preferably 14.8% by weight or less, more preferably 5% by weight or less, and even more preferably 3.2% by weight or less of at least one compound selected from the group consisting of a monoglyceryl di-fatty acid ester and a sorbitan di-fatty acid ester, (C) preferably 0.2% by weight or more, more preferably 0.4% by weight or more, and even more preferably 0.7% by weight or more, and preferably 15% by weight or less, more preferably 12% by weight or less, and even more preferably 5% by weight or less of at least one compound selected from the group consisting of a ceramide, an alcohol having 12 to 22 carbon atoms, a monoglyceryl mono-C12 to C22 fatty acid ester, a mono-C12 to C22 alkyl glyceryl ether, and a sorbitan mono-C12 to C22 fatty acid ester, and (D) water, wherein in the ingredients (A), (B), and (C), (1) a weight ratio of (A)/((B)+(C)) is 0.04 or more and preferably 0.5 or less, and more preferably 0.33 or less, (2) a mole fraction of (B)/((B)+(C)) is 0.02 or more and preferably 0.4 or less, and more preferably 0.35 or less, and (3) a maximum mole fraction of one compound as a single component in the ingredient (B) and the ingredient (C) is 0.2 or more and preferably 0.75 or less, and more preferably 0.7 or less.

[3] The emulsified cosmetic composition according to [1] or [2], wherein the ingredient (A) is preferably an ionic surfactant.

[4] The emulsified cosmetic composition according to any one of [1] to [3], wherein the ionic surfactant of the ingredient (A) is preferably at least one compound selected from the group consisting of a C12 to C22 fatty acid or a salt thereof, a polyoxyethylene C12 to C22 alkyl ether phosphoric acid or a salt thereof, a C12 to C22 N-alkyloyl methyl taurine or a salt thereof, and a N—C12 to C22 acylglutamic acid or a salt thereof, wherein a content thereof in a total composition is preferably 0.1% by weight or more, more preferably 0.2% by weight or more, and even more preferably 0.5% by weight or more, and preferably 15% by weight or less, more preferably 5% by weight or less, and even more preferably 3% by weight or less.

[5] The emulsified cosmetic composition according to [1] or [2], wherein the ingredient (A) is preferably at least one compound selected from the group consisting of a sphingosine or a salt thereof, and 1-(2-hydroxyethylamino)-3-isostearyloxy-2-propanol or a salt thereof, wherein a content thereof in a total composition is preferably 0.1% by weight or more, more preferably 0.2% by weight or more, and even more preferably 0.5% by weight or more, and preferably 15% by weight or less, more preferably 5% by weight or less, and even more preferably 3% by weight or less.

[6] The emulsified cosmetic composition according to any one of [1] to [5], wherein the ingredient (B) is preferably at least one compound selected from monoglyceryl di-fatty acid esters, wherein a content thereof in a total composition is preferably 0.1% by weight or more, more preferably 0.5% by weight or more, and even more preferably 1% by weight or more, and preferably 14.8% by weight or less, more preferably 5% by weight or less, and even more preferably 3.2% by weight or less.

[7] The emulsified cosmetic composition according to [6], wherein the monoglyceryl di-fatty acid ester of the ingredient (B) is preferably monoglyceryl distearate.

[8] The emulsified cosmetic composition according to any one of [1] to [5], wherein the ingredient (B) is preferably at least one compound selected from a sorbitan di-fatty acid ester, and wherein a content thereof in a total composition is preferably 0.1% by weight or more, more preferably 0.5% by weight or more, and even more preferably 1% by weight or more, and preferably 14.8% by weight or less, more preferably 5% by weight or less, and even more preferably 3.2% by weight or less.

[9] The emulsified cosmetic composition according to [8], wherein the sorbitan di-fatty acid ester of the ingredient (B) is preferably sorbitan distearate.

[10] The emulsified cosmetic composition according to any one of [1] to [9], wherein the ingredient (C) is preferably an alcohol having 12 to 22 carbon atoms and more preferably at least one compound selected from alcohols having 16 to 22 carbon atoms, wherein a content thereof in a total composition is preferably 0.2% by weight or more, more preferably 0.4% by weight or more, even more preferably 0.7% by weight or more, and preferably 15% by weight or less, more preferably 12% by weight or less, and even more preferably 5% by weight or less.

[11] The emulsified cosmetic composition according to [10], wherein the alcohol having 12 to 22 carbon atoms of the ingredient (C) is preferably cetanol or stearyl alcohol.

[12] The emulsified cosmetic composition according to any one of [1] to [9], wherein the ingredient (C) is preferably a monoglyceryl mono-C12 to C22 fatty acid ester and more preferably at least one compound selected from monoglyceryl mono-C16 to C22 fatty acid esters, wherein a content thereof in a total composition is preferably 0.2% by weight or more, more preferably 0.4% by weight or more, and even more preferably 0.7% by weight or more, and preferably 15% by weight or less, more preferably 12% by weight or less, and even more preferably 5% by weight or less.

[13] The emulsified cosmetic composition according to [12], wherein the monoglyceryl mono-C12 to C22 fatty acid ester of the ingredient (C) is preferably glyceryl monostearate, or glyceryl monobehenate.

[14] The emulsified cosmetic composition according to any one of [1] to [9], wherein the ingredient (C) is preferably a mono-C12 to C22 alkyl glyceryl ether, and more preferably at least one compound selected from mono-C14 to C22 alkyl glyceryl ethers, wherein a content thereof in a total composition is preferably 0.2% by weight or more, more preferably 0.4% by weight or more, and even more preferably 0.7% by weight or more, and preferably 15% by weight or less, more preferably 12% by weight or less, and even more preferably 5% by weight or less.

[15] The emulsified cosmetic composition according to [14], wherein the mono-C12 to C22 alkyl glyceryl ether of the ingredient (C) is preferably monostearyl glyceryl ether.

[16] The emulsified cosmetic composition according to any one of [1] to [9], wherein the ingredient (C) is preferably at least one compound selected from sorbitan mono-C12 to C22 fatty acid esters, wherein a content thereof in a total composition is preferably 0.2% by weight or more, more preferably 0.4% by weight or more, and even more preferably 0.7% by weight or more, and preferably 15% by weight or less, more preferably 12% by weight or less, and even more preferably 5% by weight or less.

[17] The emulsified cosmetic composition according to [16], wherein the sorbitan mono-C12 to C22 fatty acid ester of the ingredient (C) is preferably sorbitan monostearate.

[18] The emulsified cosmetic composition according to any one of [1] to [9], wherein the ingredient (C) is preferably at least one compound selected from monoglyceryl mono-C12 to C22 fatty acid esters, wherein a content thereof in a total composition is preferably 0.2% by weight or more, more preferably 0.4% by weight or more, and even more preferably 0.7% by weight or more, and preferably 15% by weight or less, more preferably 12% by weight or less, and even more preferably 5% by weight or less.

[19] The emulsified cosmetic composition according to [18], wherein the monoglyceryl mono-C12 to C22 fatty acid ester of the ingredient (C) is preferably glyceryl monobehenate.

[20] The emulsified cosmetic composition according to any one of [1] to [19], wherein a total content of the ingredients (B) and (C) in a total composition is preferably 0.5% by weight or more, and more preferably 1% by weight or more, and preferably 17% by weight or less, more preferably 10% by weight or less, and even more preferably 7% by weight or less.

[21] An emulsified cosmetic composition comprising the following ingredients (A), (B), (C), and (D):

(A) 0.2% by weight or more and 3% by weight or less of at least one compound selected from a N—C12 to C22 acylglutamic acid and a salt thereof, (B) 0.1% by weight or more and 3.2% by weight or less of at least one compound selected from sorbitan distearates, (C) 0.7% by weight or more and 5% by weight or less of at least one compound selected from the group consisting of an alcohol having 12 to 22 carbon atoms and a monoglyceryl mono-C12 to C22 fatty acid ester, and (D) water, wherein in the ingredients (A), (B), and (C), (1) a weight ratio of (A)/((B)+(C)) is 0.04 or more and 0.33 or less, (2) a mole fraction of (B)/((B)+(C)) is 0.02 or more and 0.35 or less, and (3) a maximum mole fraction of one compound as a single component in the ingredient (B) and the ingredient (C) is 0.2 or more and 0.7 or less.

EXAMPLES

Examples 1 to 26 and Comparative Examples 1 to 5

Emulsified cosmetic compositions having the formulations as shown in Tables 2 to 4 were produced. X-ray structural analysis thereof and X-ray structural analysis of dried films were performed, and storage stability, the long-lasting feeling of moisture, and the feeling of protection were evaluated. The results are shown together in Tables 2 to 4.

In Examples of the present invention and Comparative Examples, the critical packing parameter (CPP) and molecular weight of each compound in the ingredient (B) are as shown in Table 1 below.

TABLE 1

CPP and molecular weight of each compound

| Compound | Critical packing parameter (CPP) | Molecular weight |
|---|---|---|
| Glyceryl distearate | 1.58 | 650.0 |
| Pseudo-ceramide *1 | 1.37 | 598.1 |
| Sorbitan distearate | 1.14 | 697.1 |
| Cetyl alcohol | 1.07 | 242.5 |
| Stearyl alcohol | 1.07 | 270.5 |
| Monostearyl glyceryl ether | 0.63 | 430.6 |
| Glyceryl monobehenate | 0.63 | 414.7 |
| Sorbitan monostearate | 0.48 | 430.6 |

*1: N-(hexadecyloxyhydroxypropyl)-N-hydroxyethylhexadecanamide)

(Production method)

The ingredients for the first phase were mixed under heating at 80 to 95° C., and the ingredients for the second phase heated to 80 to 95° C. were then added thereto with propeller stirring (300 rpm). The resulting emulsion was gradually cooled to 25° C., whereby an emulsified cosmetic composition was obtained.

(Evaluation method)

(1) X-ray structural analysis of emulsified cosmetic compositions and X-ray structural analysis of dried films The crystal structure of each emulsified cosmetic composition was determined according to the method of Wilson and Ott (Wilson, D. A. and Ott, E., J. Chem. Phys., 2, 231-238 (1934)) from wide-angle ($2\theta$=10 to 30°) X-ray diffraction peaks immediately after production and after accelerated stability testing (a cycle of −15° C. to 60° C./day, which was performed for 7 days). The α-type structure is the hexagonal system which is characterized in that the lipophilic groups are oriented perpendicularly to the surface constituted by the hydrophilic groups and one sharp diffraction peak appears around a Bragg angle of 21 to 23°.

The results about the crystal structures of the compositions of Examples and Comparative Examples detected immediately after production are shown in "X-ray structural analysis" in the tables below. Also, the results about the crystal structures after accelerated stability testing are shown in "X-ray structural analysis of dried films" in the tables below.

(2) Storage stability

The state of each composition after 1-month storage at 50° C. and at −5° C. was evaluated by visual observation based on the following criteria:

a: Not changed.

b: Appearance and characteristics were slightly changed (change in color and changes including increase or decrease in viscosity, which however do not influence the product).

c: Appearance and characteristics were changed (change in color and increase or decrease in viscosity).

d: Appearance and characteristics were largely changed (separation or gelling, etc.).

(3) Long-lasting feeling of moisture

Ten expert panelists used each emulsified cosmetic composition and then judged the long-lasting feeling of moisture by sensory evaluation based on the following criteria:

a: Seven or more of the panelists evaluated the product as favorable (good).

b: Five or six of the panelists evaluated the product as favorable (good).

c: Three or four of the panelists evaluated the product as favorable (good).

d: Two or less of the panelists evaluated the product as favorable (good).

(4) Evaluation of feeling of protection

Ten expert panelists used each emulsified cosmetic composition and then judged the feeling of protection (a feeling like the skin was uniformly covered with something like a film) by sensory evaluation based on the following criteria:

a: Seven or more of the panelists evaluated the product as favorable (good).

b: Five or six of the panelists evaluated the product as favorable (good).

c: Three or four of the panelists evaluated the product as favorable (good).

d: Two or less of the panelists evaluated the product as favorable (good).

TABLE 2

| | | | Example | | | | | Comparative Example | | | Example | | |
|---|---|---|---|---|---|---|---|---|---|---|---|---|---|
| Ingredient (% by weight) | | | 1 | 2 | 3 | 4 | 5 | 1 | 2 | 3 | 6 | 7 | 8 |
| First phase | A | Stearoyl glutamic acid | 0.5 | 0.5 | 0.5 | 0.5 | 0.5 | 0.5 | 0.5 | 0.5 | 0.5 | 0.5 | 0.5 |
| | B | Sorbitan distearate Glyceryl distearate | 0.3 | 1 | 2 | 3 | 3.2 | | | 4 | 1 | 2 | 3 |

TABLE 2-continued

|  |  |  |  |  |  |  |  |  |  |  |  |  |
|---|---|---|---|---|---|---|---|---|---|---|---|---|
|  | C | Cetyl alcohol | 1.8 | 2.86 | 1.93 | 1.01 | 0.9 | 5 | 3.78 | 1 | 3.09 | 2.16 | 1.22 |
|  |  | Monoglyceryl behenate | 1.25 | 1.14 | 1.07 | 0.99 | 0.8 |  | 1.22 |  |  |  |  |
|  |  | Monostearyl glyceryl ether |  |  |  |  |  |  |  |  |  |  |  |
|  |  | Sorbitan monostearate |  |  |  |  |  |  |  |  | 0.91 | 0.84 | 0.78 |
| Second phase | Water |  | Balance | Balance | Balance | Balance | Balance | Balance | Balance | Balance | Balance | Balance | Balance |
|  | L-arginine |  | 0.36 | 0.36 | 0.36 | 0.36 | 0.36 | 0.36 | 0.36 | 0.36 | 0.36 | 0.36 | 0.36 |
| Total |  |  | 100 | 100 | 100 | 100 | 100 | 100 | 100 | 100 | 100 | 100 | 100 |
| Weight ratio of (A)/((B) + (C)) |  |  | 0.1 | 0.1 | 0.1 | 0.1 | 0.1 | 0.1 | 0.1 | 0.1 | 0.1 | 0.1 | 0.1 |
| Mole fraction of (B)/((B) + (C)) |  |  | 0.04 | 0.09 | 0.21 | 0.40 | 0.45 | 0.00 | 0.00 | 0.58 | 0.09 | 0.21 | 0.39 |
| Maximum mole fraction of one compound as component in the ingredients (B) + (C) |  |  | 0.68 | 0.74 | 0.59 | 0.40 | 0.45 | 1.00 | 0.84 | 0.58 | 0.44 | 0.65 | 0.45 |
| Average critical packing parameter of the ingredients (B) and (C) |  |  | 0.95 | 1.00 | 1.00 | 1.00 | 1.02 | 1.07 | 1.00 | 1.11 | 1.00 | 1.00 | 1.00 |
| Weight of (B) + (C) |  |  | 3.35 | 5.00 | 5.00 | 5.00 | 4.90 | 5.00 | 5.00 | 5.00 | 5.00 | 5.00 | 5.00 |
| Weight of (A) (excluding counterions) |  |  | 0.50 | 0.50 | 0.50 | 0.50 | 0.50 | 0.50 | 0.50 | 0.50 | 0.50 | 0.50 | 0.50 |
| Weight of (B) |  |  | 0.30 | 1.00 | 2.00 | 3.00 | 3.20 | 0.00 | 0.00 | 4.00 | 1.00 | 2.00 | 3.00 |
| Weight of (C) |  |  | 3.05 | 4.00 | 3.00 | 2.00 | 1.70 | 5.00 | 5.00 | 1.00 | 4.00 | 3.00 | 2.00 |
| Water |  |  | 95.79 | 94.14 | 94.14 | 94.14 | 94.24 | 94.14 | 94.14 | 94.14 | 94.14 | 94.14 | 94.14 |
| X-ray structural analysis |  |  | α-Type | α-Type | α-Type | α-Type | α-Type | α-Type | α-Type | α-Type | α-Type | α-Type | α-Type |
| X-ray structural analysis of dried films |  |  | α-Type | α-Type | α-Type | α-Type | α-Type | Including non-α type | Including non-α type | α-Type | α-Type | α-Type | α-Type |
| Storage stability |  |  | a | a | a | b | b | c | c | c | a | a | b |
| Long-lasting feeling of moisture |  |  | a | a | a | a | a | d | d | d | a | a | a |
| Feeling of protection |  |  | a | a | a | a | a | c | c | c | a | a | a |

|  |  |  | Comparative Example | | Example | | Example | |
|---|---|---|---|---|---|---|---|---|
| Ingredient (% by weight) |  |  | 4 | 5 | 9 | 10 | 11 | 12 |
| First phase | A | Stearoyl glutamic acid | 1.5 | 0.3 | 1.5 | 1.5 | 0.5 | 0.5 |
|  | B | Sorbitan distearate | 3 | 3 | 3 | 3 |  |  |
|  |  | Glyceryl distearate |  |  |  |  | 0.28 | 1 |
|  | C | Cetyl alcohol | 12 | 2.3 | 8.40 | 5.10 | 3.42 | 2.24 |
|  |  | Monoglyceryl behenate |  |  |  |  | 1.3 | 1.76 |
|  |  | Monostearyl glyceryl ether |  | 9.7 | 3.60 | 6.90 |  |  |
|  |  | Sorbitan monostearate |  |  |  |  |  |  |
| Second phase | Water |  | Balance | Balance | Balance | Balance | Balance | Balance |
|  | L-arginine |  | 1.08 | 0.22 | 1.08 | 1.08 | 0.36 | 0.36 |
| Total |  |  | 100 | 100 | 100 | 100 | 100 | 100 |
| Weight ratio of (A)/((B) + (C)) |  |  | 0.1 | 0.03 | 0.1 | 0.1 | 0.1 | 0.1 |
| Mole fraction of (B)/((B) + (C)) |  |  | 0.08 | 0.10 | 0.09 | 0.09 | 0.03 | 0.11 |
| Maximum mole fraction of one compound as component in the ingredients (B) + (C) |  |  | 0.92 | 0.67 | 0.70 | 0.46 | 0.80 | 0.61 |
| Average critical packing parameter of the ingredients (B) and (C) |  |  | 1.08 | 0.78 | 0.98 | 0.88 | 1.00 | 1.00 |
| Weight of (B) + (C) |  |  | 15.00 | 15.00 | 15.00 | 15.00 | 5.00 | 5.00 |
| Weight of (A) (excluding counterions) |  |  | 1.50 | 0.30 | 1.50 | 1.50 | 0.50 | 0.50 |
| Weight of (B) |  |  | 3.00 | 3.00 | 3.00 | 3.00 | 0.28 | 1.00 |
| Weight of (C) |  |  | 12.00 | 12.00 | 12.00 | 12.00 | 4.72 | 4.00 |
| Water |  |  | 82.42 | 84.48 | 82.42 | 82.42 | 94.14 | 94.14 |
| X-ray structural analysis |  |  | α-Type | α-Type | α-Type | α-Type | α-Type | α-Type |
| X-ray structural analysis of dried films |  |  | Including non-α type | Including non-α type | α-Type | α-Type | α-Type | α-Type |
| Storage stability |  |  | d | d | b | b | a | a |
| Long-lasting feeling of moisture |  |  | c | c | a | a | a | a |
| Feeling of protection |  |  | c | c | a | a | a | a |

TABLE 3

|  |  | Ingredient (% by weight) | Example 13 | 14 | 15 | 16 | 17 | 18 | 19 | 20 |
|---|---|---|---|---|---|---|---|---|---|---|
| First phase | A | Stearoyl glutamic acid | 0.2 | 0.4 | 3 | 5 | 2 | 0.1 | 0.4 | 1 |
|  |  | 1-(2-Hydroxyethylamino)-3-isostearyloxy-2-propanol |  |  |  |  |  |  |  |  |
|  |  | Phytosphingosine |  |  |  |  |  |  |  |  |
|  | B | Sorbitan distearate | 0.28 | 0.68 |  | 10.2 | 1.00 |  | 2.00 |  |
|  |  | Glyceryl distearate |  |  | 0.21 |  |  | 0.56 |  | 5 |
|  | C | Psuedo-ceramide |  |  | 1.05 |  |  |  |  |  |
|  |  | Cetyl alcohol | 0.08 | 0.216 | 3.04 | 3.24 | 2.86 | 0.14 | 0.33 | 2 |
|  |  | Stearyl alcohol |  |  |  |  |  |  | 0.05 |  |
|  |  | Monostearyl glyceryl ether | 0.14 | 0.104 | 0.70 | 1.56 |  |  |  |  |
|  |  | Glyceryl monobehenate |  |  |  |  | 1.14 |  | 0.66 |  |
|  |  | Sorbitan monostearate |  |  |  |  |  | 0.26 | 0.95 | 3 |
|  |  | Glycerol | 15 | 10 | 10 | 10 | 10 | 10 | 10 | 10 |
| Second phase | A | Water | Balance | Balance | Balance | Balance | Balance | Balance | Balance | Balance |
|  |  | Sodium POE (4) lauryl ether phosphate | 0.3 | 0.6 | 1 | 6 | 0.6 | 0.07 | 0.3 | 0.7 |
|  |  | Na lysine dilauroyl glutamate |  |  | 1 |  | 1 | 0.17 | 0.8 | 1.6 |
|  |  | Na stearoyl methyl taurine |  |  |  | 4 | 0.6 | 0.17 | 0.5 | 1.7 |
|  |  | Distearyl dimethyl ammonium chloride |  |  |  |  |  |  |  |  |
|  |  | L-arginine | 0.14 | 0.29 | 2.16 | 3.6 | 1.44 | 0.07 | 0.29 | 0.72 |
|  |  | L-glutamic acid |  |  |  |  |  |  |  |  |
| Total |  |  | 100 | 100 | 100 | 100 | 100 | 100 | 100 | 100 |

|  |  | Ingredient (% by weight) | Example 21 | 22 | 23 | 24 | 25 | 26 |
|---|---|---|---|---|---|---|---|---|
| First phase | A | Stearoyl glutamic acid | 0.1 |  | 0.4 |  |  |  |
|  |  | 1-(2-Hydroxyethylamino)-3-isostearyloxy-2-propanol |  | 0.2 |  | 0.2 | 0.13 | 0.2 |
|  |  | Phytosphingosine |  |  |  | 0.1 |  |  |
|  | B | Sorbitan distearate | 0.5 | 0.10 | 0.90 |  | 1.70 |  |
|  |  | Glyceryl distearate |  |  |  | 2.45 |  | 0.21 |
|  | C | Psuedo-ceramide |  | 0.25 | 0.38 | 1.11 |  | 1.05 |
|  |  | Cetyl alcohol | 0.1 | 0.60 | 2.70 | 11.26 | 0.54 | 3.04 |
|  |  | Stearyl alcohol | 0.01 | 0.10 |  |  |  |  |
|  |  | Monostearyl glyceryl ether |  |  | 1.30 | 0.82 | 1.98 | 0.26 | 0.7 |
|  |  | Glyceryl monobehenate |  | 0.14 |  |  |  |  |
|  |  | Sorbitan monostearate | 0.25 |  | 0.20 |  |  |  |
|  |  | Glycerol | 10 | 20 | 10 | 10 | 10 | 10 |
| Second phase | A | Water | Balance | Balance | Balance | Balance | Balance | Balance |
|  |  | Sodium POE (4) lauryl ether phosphate | 0.1 |  | 0.3 |  |  |  |
|  |  | Na lysine dilauroyl glutamate | 0.05 |  |  |  |  |  |
|  |  | Na stearoyl methyl taurine | 0.1 |  |  |  |  |  |
|  |  | Distearyl dimethyl ammonium chloride |  | 0.6 |  | 2.85 |  |  |
|  |  | L-arginine | 0.07 |  | 0.29 |  |  |  |
|  |  | L-glutamic acid |  | 0.07 |  | 0.1 | 0.05 | 0.07 |
| Total |  |  | 100 | 100 | 100 | 100 | 100 | 100 |

TABLE 4

|  | Example 13 | 14 | 15 | 16 | 17 | 18 | 19 |
|---|---|---|---|---|---|---|---|
| Weight ratio of (A)/((B) + (C)) | 0.97 | 0.97 | 0.97 | 0.97 | 0.81 | 0.50 | 0.48 |
| Mole fraction of (B)/((B) + (C)) | 0.35 | 0.45 | 0.02 | 0.45 | 0.09 | 0.40 | 0.35 |
| Maximum mole fraction of one compound as component in the ingredients (B) + (C) | 0.36 | 0.45 | 0.75 | 0.45 | 0.74 | 0.40 | 0.35 |
| Average critical packing parameter of the ingredients (B) and (C) | 0.94 | 1.04 | 1.06 | 1.04 | 1.00 | 1.12 | 0.85 |
| Weight of (B) + (C) | 0.50 | 1.00 | 5.00 | 15.00 | 5.00 | 0.96 | 3.99 |
| Weight of (A) (excluding counterions) | 0.49 | 0.97 | 4.87 | 14.50 | 4.06 | 0.48 | 1.90 |
| Weight of (B) | 0.28 | 0.68 | 0.21 | 10.20 | 1.00 | 0.56 | 2.00 |
| Weight of (C) | 0.22 | 0.32 | 4.79 | 4.80 | 4.00 | 0.40 | 1.99 |
| Water | 83.86 | 87.71 | 77.84 | 56.40 | 79.36 | 88.47 | 83.72 |
| X-ray structural analysis | α-Type | α-Type | α-Type | α-Type | α-Type | α-Type | α-Type |
| X-ray structural analysis of dried films | α-Type | α-Type | α-Type | α-Type | α-Type | α-Type | α-Type |
| Storage stability | a | a | a | b | a | a | a |
| Long-lasting feeling of moisture | c | b | b | a | a | b | a |
| Feeling of protection | c | c | b | a | b | b | b |

TABLE 4-continued

|  | Example | | | | | | |
|---|---|---|---|---|---|---|---|
|  | 20 | 21 | 22 | 23 | 24 | 25 | 26 |
| Weight ratio of (A)/((B) + (C)) | 0.48 | 0.34 | 0.33 | 0.14 | 0.18 | 0.05 | 0.04 |
| Mole fraction of (B)/((B) + (C)) | 0.394 | 0.34 | 0.02 | 0.08 | 0.07 | 0.45 | 0.02 |
| Maximum mole fraction of one compound as component in the ingredients (B) + (C) | 0.39 | 0.34 | 0.52 | 0.70 | 0.80 | 0.45 | 0.75 |
| Average critical packing parameter of the ingredients (B) and (C) | 1.07 | 0.86 | 0.86 | 1.00 | 1.07 | 1.04 | 1.06 |
| Weight of (B) + (C) | 10.00 | 1.00 | 2.35 | 5.00 | 16.80 | 2.50 | 5.00 |
| Weight of (A) (excluding counterions) | 4.75 | 0.34 | 0.76 | 0.69 | 2.98 | 0.13 | 0.20 |
| Weight of (B) | 5.00 | 0.50 | 0.10 | 0.90 | 2.45 | 1.70 | 0.21 |
| Weight of (C) | 5.00 | 0.50 | 2.25 | 4.10 | 14.35 | 0.80 | 4.79 |
| Water | 74.28 | 88.58 | 76.78 | 84.01 | 69.95 | 87.32 | 84.73 |
| X-ray structural analysis | α-Type | α-Type | α-Type | α-Type | α-Type | α-Type | α-Type |
| X-ray structural analysis of dried films | α-Type | α-Type | α-Type | α-Type | α-Type | α-Type | α-Type |
| Storage stability | b | a | a | a | c | b | a |
| Long-lasting feeling of moisture | a | b | a | a | a | a | a |
| Feeling of protection | a | a | a | a | a | a | a |

Example 27

Toning Lotion

In a similar manner to Examples 1 to 26, an emulsified cosmetic composition (toning lotion) having the composition as shown in Table 5 was produced. X-ray structural analysis was performed, and storage stability, the long-lasting feeling of moisture, and the feeling of protection were evaluated. The results are shown together in Table 5.

TABLE 5

|  |  | Ingredient (% by weight) | Example 27 |
|---|---|---|---|
| First phase | A | 1-(2-Hydroxyethylamino)-3-isostearyloxy-2-propanol | 0.2 |
|  |  | Phytosphingosine | 0.01 |
|  | B | Sorbitan distearate | 0.3 |
|  | C | Cetyl alcohol | 0.474 |
|  |  | Monostearyl glyceryl ether | 0.226 |
|  |  | Glycerol | 12 |
| Second phase | D | Water | 83.78 |
|  |  | L-glutamic acid | 0.1 |
|  |  | Methylparaben | 0.2 |
|  |  | 1,3-Butylene glycol | 1 |
|  |  | Xylitol | 1 |
|  |  | Hydroxyethyl cellulose | 0.01 |
|  |  | Eucalyptus extract | 0.1 |
|  |  | False-arborvitae tree extract | 0.1 |
|  |  | *Althea* extract | 0.1 |
|  |  | Seaweed extract | 0.1 |
|  |  | Aloe extract | 0.1 |
|  |  | Tea extract | 0.1 |
|  |  | *Houttuynia cordata* extract | 0.1 |
| Total |  |  | 100 |
| Weight ratio of (A)/((B) + (C)) |  |  | 0.21 |
| Mole fraction of (B)/((B) + (C)) |  |  | 0.15 |
| Maximum mole fraction of one compound as component in the ingredients (B) + (C) |  |  | 0.67 |
| Average critical packing parameter of the ingredients (B) and (C) |  |  | 1 |
| Weight of (B) + (C) |  |  | 1 |
| Weight of (A) (excluding counterions) |  |  | 0.6 |
| Weight of (B) |  |  | 0.3 |
| Weight of (C) |  |  | 0.7 |
| Water |  |  | 83.78 |
| X-ray structural analysis |  |  | α-Type |
| X-ray structural analysis of dried films |  |  | α-Type |
| Storage stability |  |  | a |
| Long-lasting feeling of moisture |  |  | a |
| Feeling of protection |  |  | a |

Example 28

Milky Lotion

In a similar manner to Examples 1 to 26, an emulsified cosmetic composition (milky lotion) having the composition as shown in Table 6 was produced. X-ray structural analysis was performed, and storage stability, the long-lasting feeling of moisture, and the feeling of protection were evaluated. The results are shown together in Table 6.

TABLE 6

|  |  | Ingredient (% by weight) | Example 28 |
|---|---|---|---|
| First phase | A | Stearoyl glutamic acid | 0.5 |
|  | B | Glyceryl distearate | 0.4 |
|  | C | Cetyl alcohol | 0.535 |
|  |  | Stearyl alcohol | 0.356 |
|  |  | Glyceryl monobehenate | 0.708 |
|  |  | Squalane | 4 |
|  |  | Dimethylpolysiloxane | 1 |
|  |  | Glycerol | 15 |
|  |  | POE (20) sorbitan monostearate | 0.05 |
| Second phase | D | Water | Balance |
|  |  | L-arginine | 0.36 |
|  | A | Sodium POE (4) lauryl ether phosphate | 0.1 |
|  |  | Methylparaben | 0.2 |
|  |  | 1,3-Butylene glycol | 1 |
|  |  | Trehalose | 1 |
|  |  | Ginger extract | 0.1 |
|  |  | Japanese citron (yuzu) extract | 0.1 |
|  |  | Chamomile extract | 0.1 |
|  |  | Carboxymethyl polymer | 0.2 |
|  |  | Xanthan gum | 0.1 |
|  |  | Sodium hydroxide | Amount which attains pH 7 |
| Total |  |  | 100 |
| Weight ratio of (A)/((B) + (C)) |  |  | 0.30 |
| Mole fraction of (B)/((B) + (C)) |  |  | 0.11 |
| Maximum mole fraction of one compound as component in the ingredients (B) + (C) |  |  | 0.38 |
| Weight of (B) + (C) |  |  | 2 |
| Weight of (A) (excluding counterions) |  |  | 0.595 |
| Weight of (B) |  |  | 0.4 |
| Weight of (C) |  |  | 1.599 |
| Water |  |  | — |

TABLE 6-continued

| Ingredient (% by weight) | Example 28 |
|---|---|
| X-ray structural analysis | α-Type |
| X-ray structural analysis of dried films | α-Type |
| Storage stability | a |
| Long-lasting feeling of moisture | a |
| Feeling of protection | a |

Example 29

Body Lotion

In a similar manner to Examples 1 to 26, an oil-in-water-type emulsified cosmetic composition (body lotion) having the composition as shown in Table 7 was produced. X-ray structural analysis was performed, and storage stability, the long-lasting feeling of moisture, and the feeling of protection were evaluated. The results are shown together in Table 7.

TABLE 7

| | | Ingredient (% by weight) | Example 29 |
|---|---|---|---|
| First phase | A | 1-(2-Hydroxyethylamino)-3-isostearyloxy-2-propanol | 0.2 |
| | | Phytosphingosine | 0.01 |
| | B | Sorbitan distearate | 0.5 |
| | C | Cetyl alcohol | 2.12 |
| | | Psuedo-ceramide* | 1 |
| | | Glyceryl monobehenate | 1.38 |
| | | Dimethylpolysiloxane | 5 |
| | | Vaseline | 3 |
| | | Mineral oil | 7 |
| | | Glycerol | 10 |
| Second phase | D | Water | 63.07 |
| | A | Distearyl dimethyl ammonium chloride | 0.8 |
| | | L-glutamic acid | 0.12 |
| | | Methylparaben | 0.2 |
| | | 1,3-Butylene glycol | 5 |
| | | Methyl cellulose | 0.2 |
| | | Eucalyptus extract | 0.1 |
| | | Seaweed extract | 0.1 |
| | | Aloe extract | 0.1 |
| | | *Houttuynia cordata* extract | 0.1 |
| Total | | | 100 |
| Weight ratio of (A)/((B) + (C)) | | | 0.19 |
| Mole fraction of (B)/((B) + (C)) | | | 0.05 |
| Maximum mole fraction of one compound as component in the ingredients (B) + (C) | | | 0.60 |
| Weight of (B) + (C) | | | 5 |
| Weight of (A) (excluding counterions) | | | 0.96 |
| Weight of (B) | | | 0.5 |
| Weight of (C) | | | 4.5 |
| Water | | | 63.07 |
| X-ray structural analysis | | | α-Type |
| X-ray structural analysis of dried films | | | α-Type |
| Storage stability | | | a |
| Long-lasting feeling of moisture | | | a |
| Feeling of protection | | | a |

*N-(hexadecyloxyhydroxypropyl)-N-hydroxyethylhexadecanamide

Example 30

Cream

In a similar manner to Examples 1 to 26, an oil-in-water-type emulsified cosmetic composition (cream) having the composition as shown in Table 8 was produced. X-ray structural analysis was performed, and storage stability, the long-lasting feeling of moisture, and the feeling of protection were evaluated. The results are shown together in Table 8.

TABLE 8

| | | Ingredient (% by weight) | Example 30 |
|---|---|---|---|
| First phase | A | Stearoyl glutamic acid | 0.75 |
| | B | Sorbitan distearate | 1 |
| | C | Psuedo-ceramide* | 2 |
| | | CERAMIDE 2 | 0.01 |
| | | CERAMIDE 3 | 0.01 |
| | | Cetyl alcohol | 2.11 |
| | | Sorbitan monostearate | 0.5 |
| | | Glyceryl monobehenate | 1.39 |
| | | Cholesterol | 0.05 |
| | | Phytosterol | 0.05 |
| | | Octyldodecanol | 0.5 |
| | | Pentaerythrityl tetraoctanoate | 5 |
| | | Triisopalmitin | 5 |
| | | Cholesteryl isostearate | 1 |
| | | Vaseline | 1 |
| | | Dimethylpolysiloxane | 3 |
| | | Glycerol | 20 |
| Second phase | D | Water | 55.54 |
| | A | Na stearoyl methyl taurine | 0.1 |
| | | L-arginine | 0.54 |
| | | Methylparaben | 0.2 |
| | | Polyacrylamide | 0.2 |
| | | Xanthan gum | 0.05 |
| Total | | | 100 |
| Weight ratio of (A)/((B) + (C)) | | | 0.12 |
| Mole fraction of (B)/((B) + (C)) | | | 0.08 |
| Maximum mole fraction of one compound as component in the ingredients (B) + (C) | | | 0.48 |
| Weight of (B) + (C) | | | 7 |
| Weight of (A) (excluding counterions) | | | 0.85 |
| Weight of (B) | | | 1 |
| Weight of (C) | | | 6.02 |
| Water | | | 55.54 |
| X-ray structural analysis | | | α-Type |
| X-ray structural analysis of dried films | | | α-Type |
| Storage stability | | | a |
| Long-lasting feeling of moisture | | | a |
| Feeling of protection | | | a |

*N-(hexadecyloxyhydroxypropyl)-N-hydroxyethylhexadecanamide

TABLE 9

| Formulation Example 1 | | | |
|---|---|---|---|
| | | Ingredient (% by weight) | Formulation Example 1 |
| First phase | A | Stearoyl glutamic acid | 1 |
| | B | Sorbitan distearate | 1 |
| | C | Cetyl alcohol | 3 |
| | | Psuedo-ceramide* | 1 |
| | | Glyceryl monobehenate | 2 |
| | | Dimethylpolysiloxane | 5 |
| | | Isotridecyl isononanoate | 3 |
| | | Neopentyl glycol dicaprate | 3 |
| | | Hydrogenated polyisobutene | 4 |
| | | Olive oil | 5 |
| | | Glycerol | 5 |
| Second phase | D | Water | 65.8 |
| | | L-arginine | 0.8 |
| | | Methylparaben | 0.2 |
| | | (Acrylic acid/alkyl (C10-30) acrylate) copolymer | 0.2 |
| Total | | | 100 |
| Weight ratio of (A)/((B) + (C)) | | | 0.14 |
| Mole fraction of (B)/((B) + (C)) | | | 0.07 |
| Maximum mole fraction of one compound as component in the ingredients (B) + (C) | | | 0.61 |
| Weight of (B) + (C) | | | 7 |
| Weight of (A) (excluding counterions) | | | 1 |

TABLE 9-continued

Formulation Example 1

| Ingredient (% by weight) | Formulation Example 1 |
|---|---|
| Weight of (B) | 1 |
| Weight of (C) | 6 |
| Water | 65.8 |

*N-(hexadecyloxyhydroxypropyl)-N-hydroxyethylhexadecanamide

TABLE 10

Formulation Example 2

| | | Ingredient (% by weight) | Formulation Example 2 |
|---|---|---|---|
| First phase | A | Stearoyl glutamic acid | 0.5 |
| | B | Sorbitan distearate | 0.4 |
| | C | Cetyl alcohol | 1.2 |
| | | Psuedo-ceramide* | 0.4 |
| | | Glyceryl monobehenate | 0.8 |
| | | Isopropyl palmitate | 0.5 |
| | | Cetyl dimethyl butyl ether | 0.5 |
| | | Glycerol | 1 |
| Second phase | D | Water | 93.9 |
| | | L-arginine | 0.4 |
| | | Methylparaben | 0.2 |
| | | (Acrylic acid/alkyl (C10-30) acrylate) copolymer | 0.2 |
| Total | | | 100 |
| Weight ratio of (A)/((B) + (C)) | | | 0.18 |
| Mole fraction of (B)/((B) + (C)) | | | 0.07 |
| Maximum mole fraction of one compound as component in the ingredients (B) + (C) | | | 0.61 |
| Weight of (B) + (C) | | | 3 |
| Weight of (A) (excluding counterions) | | | 0.5 |
| Weight of (B) | | | 0.4 |
| Weight of (C) | | | 2.4 |
| Water | | | 93.9 |

*N-(hexadecyloxyhydroxypropyl)-N-hydroxyethylhexadecanamide

What is claimed is:

1. An emulsified cosmetic composition comprising the following ingredients (A), (B), (C), and (D):
   (A) 0.1% by weight or more and 15% by weight or less of at least one compound selected from the group consisting of a sphingosine or a salt thereof, a pseudo-sphingosine or a salt thereof, and an ionic surfactant,
   (B) at least one compound selected from the group consisting of a monoglyceryl di-fatty acid ester and a sorbitan di-fatty acid ester,
   (C) at least one compound selected from the group consisting of a ceramide, an alcohol having 12 to 22 carbon atoms, a monoglyceryl mono-C12 to C22 fatty acid ester, a mono-C12 to C22 alkyl glyceryl ether, and a sorbitan mono-C12 to C22 fatty acid ester, except that
     (i) ingredient (C) does not comprise both a ceramide and an alcohol having 12 to 22 carbon atoms; and
     (ii) if ingredient (C) comprises a ceramide, then the composition does not comprise a sterol,
   and
   (D) water,
   wherein, in the ingredients (A), (B), and (C),
     (1) a weight ratio of (A)/(B+C) is 0.04 or more and 1 or less,
     (2) a mole fraction of (B)/(B+C) is 0.02 or more and 0.45 or less, and
     (3) a maximum mole fraction of one compound as a single ingredient in the ingredient (B) and the ingredient (C) is 0.2 or more and 0.8 or less.

2. The emulsified cosmetic composition according to claim 1, wherein a total content of the ingredients (B) and (C), (B)+(C), is 1% by weight or more and 17% by weight or less.

3. The emulsified cosmetic composition according to claim 1, wherein the total number of compound species constituting the ingredient (B) and the ingredient (C) is three or more.

4. The emulsified cosmetic composition according to claim 1, wherein an average critical packing parameter of the ingredients (B) and (C) is 0.85 or more and 1.1 or less.

5. The emulsified cosmetic composition according to claim 1, wherein the ingredient (A) is an anionic surfactant.

6. The emulsified cosmetic composition according to claim 1, wherein the ingredient (A) is at least one compound selected from the group consisting of a C12 to C22 fatty acid salt, a N-C12 to C22 acylglutamic acid salt, a polyoxyethylene C12 to C22 alkyl ether phosphoric acid salt, and a C12 to C22 N-alkyloyl methyl taurine salt.

7. The emulsified cosmetic composition according to claim 1, wherein the ingredient (C) is at least one compound selected from the group consisting of an alcohol having 12 to 22 carbon atoms and a monoglyceryl mono-C12 to C22 fatty acid ester.

8. The emulsified cosmetic composition according to claim 1, wherein the ingredient (C) is at least one compound selected from the group consisting of cetanol, stearyl alcohol, and glyceryl monobehenate.

9. The emulsified cosmetic composition according to claim 1, wherein the composition further comprises (E) a polyhydric alcohol.

10. The emulsified cosmetic composition according to claim 9, in which the content of the polyhydric alcohol is 1%-30% by weight.

11. The emulsified cosmetic composition according to claim 10, in which the content of the polyhydric alcohol is 5%-20% by weight.

12. A method for moisturizing a skin, comprising applying the emulsified cosmetic composition according to claim 1 to the skin and then letting it to dry to thereby form a film having an α-gel structure.

* * * * *